United States Patent
Yuen et al.

(10) Patent No.: US 9,241,635 B2
(45) Date of Patent: Jan. 26, 2016

(54) PORTABLE MONITORING DEVICES FOR PROCESSING APPLICATIONS AND PROCESSING ANALYSIS OF PHYSIOLOGICAL CONDITIONS OF A USER ASSOCIATED WITH THE PORTABLE MONITORING DEVICE

(71) Applicant: Fitbit, Inc., San Francisco, CA (US)

(72) Inventors: Shelten Gee Jao Yuen, Berekely, CA (US); James Park, Berekely, CA (US); Eric Nathan Friedman, San Francisco, CA (US); Mark Manuel Martinez, San Francisco, CA (US); Andrew Cole Axely, San Francisco, CA (US)

(73) Assignee: Fitbit, Inc., San Francisco, CA (US)

( * ) Notice: Subject to any disclaimer, the term of this patent is extended or adjusted under 35 U.S.C. 154(b) by 67 days.

(21) Appl. No.: 14/156,413

(22) Filed: Jan. 15, 2014

(65) Prior Publication Data

US 2014/0135612 A1      May 15, 2014

Related U.S. Application Data

(60) Continuation-in-part of application No. 13/959,714, filed on Aug. 5, 2013, now Pat. No. 8,762,101, which is a continuation-in-part of application No. 13/693,334, filed on Dec. 4, 2012, now Pat. No.

(Continued)

(51) Int. Cl.
*G06F 19/00* (2011.01)
*A61B 5/00* (2006.01)

(Continued)

(52) U.S. Cl.
CPC ............ *A61B 5/0059* (2013.01); *A61B 5/0022* (2013.01); *A61B 5/01* (2013.01);

(Continued)

(58) Field of Classification Search
CPC . A61B 5/0022; A61B 5/1118; A61B 5/02055
USPC ................ 702/160, 150, 155, 182–185, 188
See application file for complete search history.

(56) References Cited

U.S. PATENT DOCUMENTS

| 2,284,849 A | 8/1941 | Anderson et al. |
| 2,717,736 A | 9/1955 | Schlesinger |

(Continued)

FOREIGN PATENT DOCUMENTS

| JP | 11347021 | 12/1999 |
| WO | WO 2008/038141 | 4/2008 |
| WO | WO 2009/042965 | 4/2009 |

OTHER PUBLICATIONS

Deepak et al., Plug-and-Play, Single-Chip Photoplethysmography, 34th Annual International Conference of the IEEE EMBS, San Diego, California USA, Aug. 28-Sep. 1, 2012, 4 pages.

(Continued)

*Primary Examiner* — Edward Raymond
(74) *Attorney, Agent, or Firm* — Martine Penilla Group, LLP

(57) ABSTRACT

An activity monitoring device and associated methods for using and interfacing with the activity monitoring device are provided. In one example, the activity monitoring device includes a housing configured for attachment to a body part of a user. Also included ins a display screen attached to the housing and a sensor for capturing physiological conditions of the user. The sensor is disposed along a surface of the housing so that the sensor is proximate to the body part, the body part having at least some exposed skin. The activity monitoring device also includes memory for storing the captured physiological conditions, and a processor for examining the captured physiological conditions. At a particular time, the processor automatically selects an application to execute from a plurality of applications based on characteristics of the captured physiological conditions.

17 Claims, 31 Drawing Sheets

Related U.S. Application Data 8,548,770, which is a division of application No. 13/667,229, filed on Nov. 2, 2012, now Pat. No. 8,437,980, which is a division of application No. 13/469,027, filed on May 10, 2012, now Pat. No. 8,311,769, which is a division of application No. 13/246,843, filed on Sep. 27, 2011, now Pat. No. 8,180,591, which is a division of application No. 13/156,304, filed on Jun. 8, 2011, application No. 14/156,413, which is a continuation-in-part of application No. 13/959,714, which is a continuation-in-part of application No. 13/759,485, filed on Feb. 5, 2013, now Pat. No. 8,543,351, which is a division of application No. 13/667,229, which is a division of application No. 13/469,027, which is a division of application No. 13/246,843, which is a division of application No. 13/156,304, application No. 14/156,413, which is a continuation-in-part of application No. 13/959,719, filed on Aug. 5, 2013, now Pat. No. 8,712,724.

(60) Provisional application No. 61/388,595, filed on Sep. 30, 2010, provisional application No. 61/390,811, filed on Oct. 7, 2010, provisional application No. 61/752,826, filed on Jan. 15, 2013.

(51) Int. Cl.
| | |
|---|---|
| A61B 5/11 | (2006.01) |
| A61B 5/01 | (2006.01) |
| A61B 5/024 | (2006.01) |
| A61B 5/0205 | (2006.01) |
| A61B 5/021 | (2006.01) |
| A61B 5/22 | (2006.01) |
| G01C 22/00 | (2006.01) |

(52) U.S. Cl.
CPC .......... *A61B 5/0205* (2013.01); *A61B 5/02405* (2013.01); *A61B 5/112* (2013.01); *A61B 5/1112* (2013.01); *A61B 5/1118* (2013.01); *A61B 5/441* (2013.01); *A61B 5/681* (2013.01); *A61B 5/6838* (2013.01); *A61B 5/021* (2013.01); *A61B 5/02055* (2013.01); *A61B 5/02416* (2013.01); *A61B 5/222* (2013.01); *A61B 5/4809* (2013.01); *A61B 5/4812* (2013.01); *A61B 5/4815* (2013.01); *A61B 5/7264* (2013.01); *A61B 5/743* (2013.01); *A61B 2560/0214* (2013.01); *A61B 2560/0242* (2013.01); *A61B 2562/0219* (2013.01); *G01C 22/006* (2013.01); *G06F 19/3406* (2013.01); *G06F 19/3481* (2013.01)

(56) References Cited

U.S. PATENT DOCUMENTS

| | | |
|---|---|---|
| 2,883,255 A | 4/1959 | Anderson |
| 3,163,856 A | 12/1964 | Kirby |
| 3,250,270 A | 5/1966 | Bloom |
| 3,918,658 A | 11/1975 | Beller |
| 4,192,000 A | 3/1980 | Lipsey |
| 4,244,020 A | 1/1981 | Ratcliff |
| 4,281,663 A | 8/1981 | Pringle |
| 4,284,849 A | 8/1981 | Anderson et al. |
| 4,312,358 A | 1/1982 | Barney |
| 4,367,752 A | 1/1983 | Jimenez et al. |
| 4,390,922 A | 6/1983 | Pelliccia |
| 4,407,295 A | 10/1983 | Steuer et al. |
| 4,425,921 A | 1/1984 | Fujisaki et al. |
| 4,575,804 A | 3/1986 | Ratcliff |
| 4,578,769 A | 3/1986 | Frederick |
| 4,617,525 A | 10/1986 | Lloyd |
| 4,887,249 A | 12/1989 | Thinesen |
| 4,977,509 A | 12/1990 | Pitchford et al. |
| 5,058,427 A | 10/1991 | Brandt |
| 5,224,059 A | 6/1993 | Nitta et al. |
| 5,295,085 A | 3/1994 | Hoffacker |
| 5,323,650 A | 6/1994 | Fullen et al. |
| 5,446,705 A | 8/1995 | Haas et al. |
| 5,456,648 A | 10/1995 | Edinburg et al. |
| 5,583,776 A | 12/1996 | Levi et al. |
| 5,671,162 A | 9/1997 | Werbin |
| 5,704,350 A | 1/1998 | Williams, III |
| 5,724,265 A | 3/1998 | Hutchings |
| 5,890,128 A | 3/1999 | Diaz et al. |
| 5,891,042 A | 4/1999 | Sham et al. |
| 5,894,454 A | 4/1999 | Kondo |
| 5,899,963 A | 5/1999 | Hutchings |
| 5,947,868 A | 9/1999 | Dugan |
| 5,955,667 A | 9/1999 | Fyfe |
| 5,976,083 A | 11/1999 | Richardson et al. |
| 6,018,705 A | 1/2000 | Gaudet et al. |
| 6,077,193 A | 6/2000 | Buhler et al. |
| 6,085,248 A | 7/2000 | Sambamurthy et al. |
| 6,129,686 A | 10/2000 | Friedman |
| 6,145,389 A | 11/2000 | Ebeling et al. |
| 6,183,425 B1 | 2/2001 | Whalen et al. |
| 6,213,872 B1 | 4/2001 | Harada et al. |
| 6,241,684 B1 | 6/2001 | Amano et al. |
| 6,287,262 B1 | 9/2001 | Amano et al. |
| 6,301,964 B1 | 10/2001 | Fyfe et al. |
| 6,302,789 B2 | 10/2001 | Harada et al. |
| 6,305,221 B1 | 10/2001 | Hutchings |
| 6,309,360 B1 | 10/2001 | Mault |
| 6,469,639 B2 | 10/2002 | Tanenhaus et al. |
| 6,478,736 B1 | 11/2002 | Mault |
| 6,513,381 B2 | 2/2003 | Fyfe et al. |
| 6,513,532 B2 | 2/2003 | Mault et al. |
| 6,527,711 B1 | 3/2003 | Stivoric et al. |
| 6,529,827 B1 | 3/2003 | Beason et al. |
| 6,561,951 B2 | 5/2003 | Cannon et al. |
| 6,571,200 B1 | 5/2003 | Mault |
| 6,585,622 B1 | 7/2003 | Shum et al. |
| 6,607,493 B2 | 8/2003 | Song |
| 6,620,078 B2 | 9/2003 | Pfeffer |
| 6,678,629 B2 | 1/2004 | Tsuji |
| 6,699,188 B2 | 3/2004 | Wessel |
| 6,761,064 B2 | 7/2004 | Tsuji |
| 6,790,178 B1 | 9/2004 | Mault et al. |
| 6,808,473 B2 | 10/2004 | Hisano et al. |
| 6,811,516 B1 | 11/2004 | Dugan |
| 6,813,582 B2 | 11/2004 | Levi et al. |
| 6,813,931 B2 | 11/2004 | Yadav et al. |
| 6,856,938 B2 | 2/2005 | Kurtz |
| 6,862,575 B1 | 3/2005 | Anttila et al. |
| 7,062,225 B2 | 6/2006 | White |
| 7,162,368 B2 | 1/2007 | Levi et al. |
| 7,171,331 B2 | 1/2007 | Vock et al. |
| 7,200,517 B2 | 4/2007 | Darley et al. |
| 7,246,033 B1 | 7/2007 | Kudo |
| 7,261,690 B2 | 8/2007 | Teller et al. |
| 7,272,982 B2 | 9/2007 | Neuhauser et al. |
| 7,373,820 B1 | 5/2008 | James |
| 7,443,292 B2 | 10/2008 | Jensen et al. |
| 7,457,724 B2 | 11/2008 | Vock et al. |
| 7,467,060 B2 | 12/2008 | Kulach et al. |
| 7,505,865 B2 | 3/2009 | Ohkubo et al. |
| 7,559,877 B2 | 7/2009 | Parks et al. |
| 7,653,508 B1 | 1/2010 | Kahn et al. |
| 7,690,556 B1 | 4/2010 | Kahn et al. |
| 7,713,173 B2 | 5/2010 | Shin et al. |
| 7,762,952 B2 | 7/2010 | Lee et al. |
| 7,774,156 B2 | 8/2010 | Niva et al. |
| 7,789,802 B2 | 9/2010 | Lee et al. |
| 7,881,902 B1 | 2/2011 | Kahn et al. |
| 7,927,253 B2 | 4/2011 | Vincent et al. |
| 7,983,876 B2 | 7/2011 | Vock et al. |
| 8,028,443 B2 | 10/2011 | Case, Jr. |
| 8,055,469 B2 | 11/2011 | Kulach et al. |
| 8,099,318 B2 | 1/2012 | Moukas et al. |
| 8,177,260 B2 | 5/2012 | Tropper et al. |

(56) References Cited

U.S. PATENT DOCUMENTS

| | | | |
|---|---|---|---|
| 8,180,591 B2 | 5/2012 | Yuen et al. |
| 8,180,592 B2 | 5/2012 | Yuen et al. |
| 8,311,769 B2 | 11/2012 | Yuen et al. |
| 8,311,770 B2 | 11/2012 | Yuen et al. |
| 8,386,008 B2 | 2/2013 | Yuen et al. |
| 8,437,980 B2 | 5/2013 | Yuen et al. |
| 8,463,576 B2 | 6/2013 | Yuen et al. |
| 8,463,577 B2 | 6/2013 | Yuen et al. |
| 8,543,185 B2 | 9/2013 | Yuen et al. |
| 8,543,351 B2 | 9/2013 | Yuen et al. |
| 8,548,770 B2 | 10/2013 | Yuen et al. |
| 8,583,402 B2 | 11/2013 | Yuen et al. |
| 8,597,093 B2 | 12/2013 | Engelberg et al. |
| 8,670,953 B2 | 3/2014 | Yuen et al. |
| 2001/0055242 A1 | 12/2001 | Deshmukh et al. |
| 2002/0013717 A1 | 1/2002 | Ando et al. |
| 2002/0077219 A1 | 6/2002 | Cohen et al. |
| 2002/0082144 A1 | 6/2002 | Pfeffer |
| 2002/0109600 A1 | 8/2002 | Mault et al. |
| 2002/0178060 A1 | 11/2002 | Sheehan |
| 2002/0198776 A1 | 12/2002 | Nara et al. |
| 2003/0018523 A1 | 1/2003 | Rappaport et al. |
| 2003/0050537 A1 | 3/2003 | Wessel |
| 2003/0065561 A1 | 4/2003 | Brown et al. |
| 2003/0131059 A1 | 7/2003 | Brown et al. |
| 2004/0054497 A1 | 3/2004 | Kurtz |
| 2004/0061324 A1 | 4/2004 | Howard |
| 2004/0117963 A1 | 6/2004 | Schneider |
| 2004/0152957 A1 | 8/2004 | Stivoric et al. |
| 2005/0037844 A1 | 2/2005 | Shum et al. |
| 2005/0038679 A1 | 2/2005 | Short |
| 2005/0054938 A1 | 3/2005 | Wehman et al. |
| 2005/0102172 A1 | 5/2005 | Sirmans, Jr. |
| 2005/0107723 A1 | 5/2005 | Wehman et al. |
| 2005/0228244 A1 | 10/2005 | Banet |
| 2005/0228692 A1 | 10/2005 | Hodgdon |
| 2005/0234742 A1 | 10/2005 | Hodgdon |
| 2005/0248718 A1 | 11/2005 | Howell et al. |
| 2005/0272564 A1 | 12/2005 | Pyles et al. |
| 2006/0020177 A1 | 1/2006 | Seo et al. |
| 2006/0025282 A1 | 2/2006 | Redmann |
| 2006/0047208 A1 | 3/2006 | Yoon |
| 2006/0047447 A1 | 3/2006 | Brady et al. |
| 2006/0089542 A1 | 4/2006 | Sands |
| 2006/0111944 A1 | 5/2006 | Sirmans, Jr. et al. |
| 2006/0129436 A1 | 6/2006 | Short |
| 2006/0143645 A1 | 6/2006 | Vock et al. |
| 2006/0277474 A1 | 12/2006 | Robarts et al. |
| 2006/0282021 A1 | 12/2006 | DeVaul et al. |
| 2006/0287883 A1 | 12/2006 | Turgiss et al. |
| 2007/0050715 A1 | 3/2007 | Behar |
| 2007/0051369 A1 | 3/2007 | Choi et al. |
| 2007/0071643 A1 | 3/2007 | Hall et al. |
| 2007/0123391 A1 | 5/2007 | Shin et al. |
| 2007/0136093 A1 | 6/2007 | Rankin et al. |
| 2007/0155277 A1 | 7/2007 | Amitai et al. |
| 2007/0159926 A1 | 7/2007 | Prstojevich et al. |
| 2007/0179356 A1 | 8/2007 | Wessel |
| 2007/0194066 A1 | 8/2007 | Ishihara et al. |
| 2007/0197920 A1 | 8/2007 | Adams |
| 2007/0208544 A1 | 9/2007 | Kulach et al. |
| 2007/0276271 A1 | 11/2007 | Chan |
| 2008/0093838 A1 | 4/2008 | Tropper et al. |
| 2008/0125288 A1 | 5/2008 | Case |
| 2008/0140163 A1 | 6/2008 | Keacher et al. |
| 2008/0140338 A1 | 6/2008 | No et al. |
| 2008/0146892 A1* | 6/2008 | LeBoeuf et al. ............... 600/300 |
| 2009/0018797 A1 | 1/2009 | Kasama et al. |
| 2009/0043531 A1 | 2/2009 | Kahn et al. |
| 2009/0048044 A1 | 2/2009 | Oleson et al. |
| 2009/0054737 A1 | 2/2009 | Magar et al. |
| 2009/0063193 A1 | 3/2009 | Barton et al. |
| 2009/0171788 A1 | 7/2009 | Tropper et al. |
| 2009/0271147 A1 | 10/2009 | Sugai |
| 2010/0205541 A1 | 8/2010 | Rapaport et al. |
| 2010/0217099 A1 | 8/2010 | LeBoeuf et al. |
| 2011/0003665 A1 | 1/2011 | Burton et al. |
| 2011/0009051 A1 | 1/2011 | Khedouri et al. |
| 2011/0022349 A1 | 1/2011 | Stirling et al. |
| 2011/0080349 A1 | 4/2011 | Holbein et al. |
| 2011/0106449 A1 | 5/2011 | Chowdhary et al. |
| 2011/0131005 A1 | 6/2011 | Ueshima et al. |
| 2011/0193704 A1 | 8/2011 | Harper et al. |
| 2011/0224508 A1 | 9/2011 | Moon |
| 2011/0230729 A1 | 9/2011 | Shirasaki et al. |
| 2012/0072165 A1 | 3/2012 | Jallon |
| 2012/0083705 A1 | 4/2012 | Yuen et al. |
| 2012/0083714 A1 | 4/2012 | Yuen et al. |
| 2012/0083715 A1 | 4/2012 | Yuen et al. |
| 2012/0083716 A1 | 4/2012 | Yuen et al. |
| 2012/0084053 A1 | 4/2012 | Yuen et al. |
| 2012/0084054 A1 | 4/2012 | Yuen et al. |
| 2012/0092157 A1 | 4/2012 | Tran |
| 2012/0183939 A1 | 7/2012 | Aragones et al. |
| 2012/0226471 A1 | 9/2012 | Yuen et al. |
| 2012/0226472 A1 | 9/2012 | Yuen et al. |
| 2012/0227737 A1 | 9/2012 | Mastrototaro et al. |
| 2012/0265480 A1 | 10/2012 | Oshima |
| 2012/0330109 A1 | 12/2012 | Tran |
| 2013/0006718 A1 | 1/2013 | Nielsen et al. |
| 2013/0072169 A1 | 3/2013 | Ross et al. |
| 2013/0073254 A1 | 3/2013 | Yuen et al. |
| 2013/0073255 A1 | 3/2013 | Yuen et al. |
| 2013/0080113 A1 | 3/2013 | Yuen et al. |
| 2013/0095459 A1 | 4/2013 | Tran |
| 2013/0096843 A1 | 4/2013 | Yuen et al. |
| 2013/0151196 A1 | 6/2013 | Yuen et al. |
| 2013/0158369 A1 | 6/2013 | Yuen et al. |
| 2013/0231574 A1 | 9/2013 | Tran |
| 2013/0261475 A1 | 10/2013 | Mochizuki |
| 2013/0267249 A1 | 10/2013 | Rosenberg |
| 2013/0268199 A1 | 10/2013 | Nielsen et al. |
| 2013/0268236 A1 | 10/2013 | Yuen et al. |
| 2013/0296666 A1 | 11/2013 | Kumar et al. |
| 2013/0296673 A1 | 11/2013 | Thaveeprungsriporn et al. |
| 2013/0310896 A1 | 11/2013 | Mass |
| 2013/0325396 A1 | 12/2013 | Yuen et al. |
| 2014/0035761 A1 | 2/2014 | Burton et al. |
| 2014/0039804 A1 | 2/2014 | Park et al. |
| 2014/0039840 A1 | 2/2014 | Yuen et al. |
| 2014/0077673 A1 | 3/2014 | Garg et al. |

OTHER PUBLICATIONS

"Automatic classification of ambulatory movements and evaluation of energy consumptions utilizing accelerometers and barometer", Ohtaki, et al, Microsystem Technologies, vol. 11, No. 8-10, Aug. 2005, pp. 1034-1040.

"Classification of Human Moving Patterns Using Air Pressure and Acceleration", Sagawa, et al, Proceedings of the 24$^{th}$ Annual Conference of the IEEE Industrial Electronics Society, vol. 2, Aug.-Sep. 1998, pp. 1214-1219.

"Non-restricted measurement of walking distance", Sagawa, et al, IEEE Int' l Conf. on Systems, Man, and Cybernetics, vol. 3, Oct. 2000, pp. 1847-1852.

"Activity Classification Using Realistic Data From Wearable Sensors", Parkka, et al, IEEE Transactions on Information Technology in Biomedicine, vol. 10, No. 1, Jan. 2006, pp. 119-128.

"Indoor Navigation with MEMS Sensors", Lammel, et al., Proceedings of the Eurosensors XIII conference, vol. 1, No. 1, Sep. 2009, pp. 532-535.

"Design of a Wireless Assisted Pedestrian Dead Reckoning System—The NavMote Experience", Fang, et al, IEEE Transactions on Instrumentation and Measurement, vol. 54, No. 6, Dec. 2005, pp. 2342-2358.

"On Foot Navigation: When GPS alone is not Enough", Ladetto, et al, Journal of Navigation, vol. 53, No. 2, Sep. 2000, pp. 279-285.

"A Hybrid Discriminative/Generative Approach for Modeling Human Activities", Lester, et al., Proc. of the Int'l Joint Conf. Artificial Intelligence, 2005, pp. 766-772.

"Using MS5534 for altimeters and barometers", Intersema App., Note AN501, Jan. 2006.

(56) References Cited

OTHER PUBLICATIONS

"Validated caloric expenditure estimation using a single body-worn sensor", Lester, et al, Proc. of the Int'l Conf. on Ubiquitous Computing, 2009, pp. 225-234.

"Drift-free dynamic height sensor using MEMS IMU aided by MEMS pressure sensor", Tanigawa, et al, Workshop on Positioning, Navigation and Communication, Mar. 2008, pp. 191-196.

"Improvement of Walking Speed Prediction by Accelerometry and Altimetry, Validated by Satellite Positioning", Perrin, et al, Medical & Biological Engineering & Computing, vol. 38, 2000, pp. 164-168.

"An Intelligent Multi-Sensor system for Pedestrian Navigation", Retscher, Journal of Global Positioning Systems, vol. 5, No. 1, 2006, pp. 110-118.

"Evaluation of a New Method of Heading Estimation of Pedestrian Dead Reckoning Using Shoe Mounted Sensors", Stirling et al., Journal of Navigation, vol. 58, 2005, pp. 31-45.

"Direct Measurement of Human Movement by Accelerometry", Godfrey, et al., Medical Engineering & Physics, vol. 30, 2008, pp. 1364-1386.

"Foot Mounted Inertia System for Pedestrian Naviation", Godha et al., Measurement Science and Technology, vol. 19, No. 7, May 2008, pp. 1-9.

"Altimeter and Barometer System", Clifford, et al., Freescale Semiconductor Aplication Note AN1979, Rev. 3, Nov. 2006.

"SCP 1000-D01/D11 Pressure Sensor as Barometer and Altimeter", VTI Technologies Application, Jun. 2006, Note 33.

"Suunto LUMI User Guide", Jun. and Sep. 1997.

International Search Report issued on Aug. 15, 2008, in related application PCT/IB07/03617.

* cited by examiner

PORTABLE MONITORING DEVICES FOR PROCESSING APPLICATIONS AND PROCESSING ANALYSIS OF PHYSIOLOGICAL CONDITIONS OF A USER ASSOCIATED WITH THE PORTABLE MONITORING DEVICE

CLAIM OF PRIORITY

This Application claims priority from U.S. Provisional Application No. 61/752,826, filed on Jan. 15, 2013, and entitled "Portable Monitoring Devices and Methods of Operating Same," which is herein incorporated by reference.

This application is also a continuation-in-part of U.S. patent application Ser. No. 13/959,714, filed on Aug. 5, 2013, titled "Methods and Systems for Identification of Event Data Having Combined Activity and Location Information of Portable Monitoring Devices", which is a continuation-in-part of U.S. patent application Ser. No. 13/693,334 (now issued as U.S. Pat. No. 8,548,770, issued on Oct. 1, 2013), filed on Dec. 4, 2012, titled "Portable Monitoring Devices and Methods for Operating Same", which is a divisional of U.S. patent application Ser. No. 13/667,229 (now issued as U.S. Pat. No. 8,437,980, issued on May 7, 2013), filed on Nov. 2, 2012, titled "Portable Monitoring Devices and Methods for Operating Same", which is a divisional of U.S. patent application Ser. No. 13/469,027, now U.S. Pat. No. 8,311,769, filed on May 10, 2012, titled "Portable Monitoring Devices and Methods for Operating Same", which is a divisional of U.S. patent application Ser. No. 13/246,843, now U.S. Pat. No. 8,180,591, filed on Sep. 27, 2011, which is a divisional of U.S. patent application Ser. No. 13/156,304, filed on Jun. 8, 2011, titled "Portable Monitoring Devices and Methods for Operating Same", which claims the benefit of and priority to, under 35 U.S.C. 119§(e), to U.S. Provisional Patent Application No. 61/388,595, filed on Sep. 30, 2010, and titled "Portable Monitoring Devices and Methods for Operating Same", and to U.S. Provisional Patent Application No. 61/390,811, filed on Oct. 7, 2010, and titled "Portable Monitoring Devices and Methods for Operating Same", all of which are hereby incorporated by reference in their entirety.

This application is a continuation-in-part of Ser. No. 13/959,714, filed Aug. 5, 2013, titled "Methods and Systems for Identification of Event Data Having Combined Activity and Location Information of Portable Monitoring Devices", which is a continuation-in-part of U.S. patent application Ser. No. 13/759,485 (now issued as U.S. Pat. No. 8,543,351, issued on Sep. 24, 2013), filed on Feb. 5, 2013, titled "Portable Monitoring Devices and Methods for Operating Same", which is a divisional of U.S. patent application Ser. No. 13/667,229, filed on Nov. 2, 2012, titled "Portable Monitoring Devices and Methods for Operating Same", which is a divisional of U.S. patent application Ser. No. 13/469,027, now U.S. Pat. No. 8,311,769, filed on May 10, 2012, titled "Portable Monitoring Devices and Methods for Operating Same", which is a divisional of U.S. patent application Ser. No. 13/246,843, now U.S. Pat. No. 8,180,591, filed on Sep. 27, 2011, which is a divisional of U.S. patent application Ser. No. 13/156,304, filed on Jun. 8, 2011, titled "Portable Monitoring Devices and Methods for Operating Same", which claims the benefit of and priority to, under 35 U.S.C. 119§(e), to U.S. Provisional Patent Application No. 61/388,595, filed on Sep. 30, 2010, and titled "Portable Monitoring Devices and Methods for Operating Same" and to U.S. Provisional Patent Application No. 61/390,811, filed on Oct. 7, 2010, and titled "Portable Monitoring Devices and Methods for Operating Same", all of which are hereby incorporated by reference in their entirety.

This application is a continuation of U.S. patent application Ser. No. 13/959,719, filed on Aug. 5, 2013, titled "Calendar Integration Methods and Systems for Presentation of Events Having Combined Activity and Location Information", which is incorporated by reference herein in its entirety.

FIELD

The present disclosure relates to systems and methods for linking communication between an activity tracking device and a client device.

BACKGROUND

In recent years, the need for health and fitness has grown tremendously. The growth has occurred due to a better understanding of the benefits of good fitness to overall health and wellness. Unfortunately, although today's modern culture has brought about many new technologies, such as the Internet, connected devices and computers, people have become less active. Additionally, many office jobs require people to sit in front of computer screens for long periods of time, which further reduces a person's activity levels. Furthermore, much of today's entertainment options involve viewing multimedia content, computer social networking, and other types of computer involved interfacing. Although such computer activity can be very productive as well as entertaining, such activity tends to reduce a person's overall physical activity.

To provide users concerned with health and fitness a way of measuring or accounting for their activity or lack thereof, fitness trackers are often used. Fitness trackers are used to measure activity, such as walking, motion, running, sleeping, being inactive, bicycling, exercising on an elliptical trainer, and the like. Usually, the data collected by such fitness trackers can be transferred and viewed on a computing device. However, such data is often provided as a basic accumulation of activity data with complicated or confusing interfaces. In addition, updates between a tracker and a client device usually require wired connectors and/or complex syncing schemes.

It is in this context that embodiments described herein arise.

SUMMARY

Embodiments described in the present disclosure provide systems, apparatus, computer readable media, and methods.

In one embodiment, an activity monitoring device and associated methods for using and interfacing with the activity monitoring device are provided. In one example, the activity monitoring device includes a housing configured for attachment to a body part of a user. Also included ins a display screen attached to the housing and a sensor for capturing physiological conditions of the user. The sensor is disposed along a surface of the housing so that the sensor is proximate to the body part, the body part having at least some exposed skin. The activity monitoring device also includes memory for storing the captured physiological conditions, and a processor for examining the captured physiological conditions. At a particular time, the processor automatically selects an application to execute from a plurality of applications based on characteristics of the captured physiological conditions.

In another embodiment, an activity monitoring device is provided. The device includes a wrist band and a display screen disposed on a housing. The wrist band is coupled to the housing. A sensor is disposed in the housing to capture data associated with a user. Memory is disposed in the housing for storing the captured data and for storing one or more applications. Further provided is a processor that is in communication with the housing and the display screen. The processor is configured to execute the one or more applications to render content associated with the one or more applications on the display screen, at least one of the applications being configured to present metric regarding the captured data of the sensor. The captured data including one of motion data by the user, environmental data, biometric data of the user, or combinations of two or more thereof, and the processor enables a user to access the one or more applications to cause rendering of a user interface on the display screen.

BRIEF DESCRIPTION OF THE DRAWINGS

Various embodiments described in the present disclosure may best be understood by reference to the following description taken in conjunction with the accompanying drawings.

Figure 1:
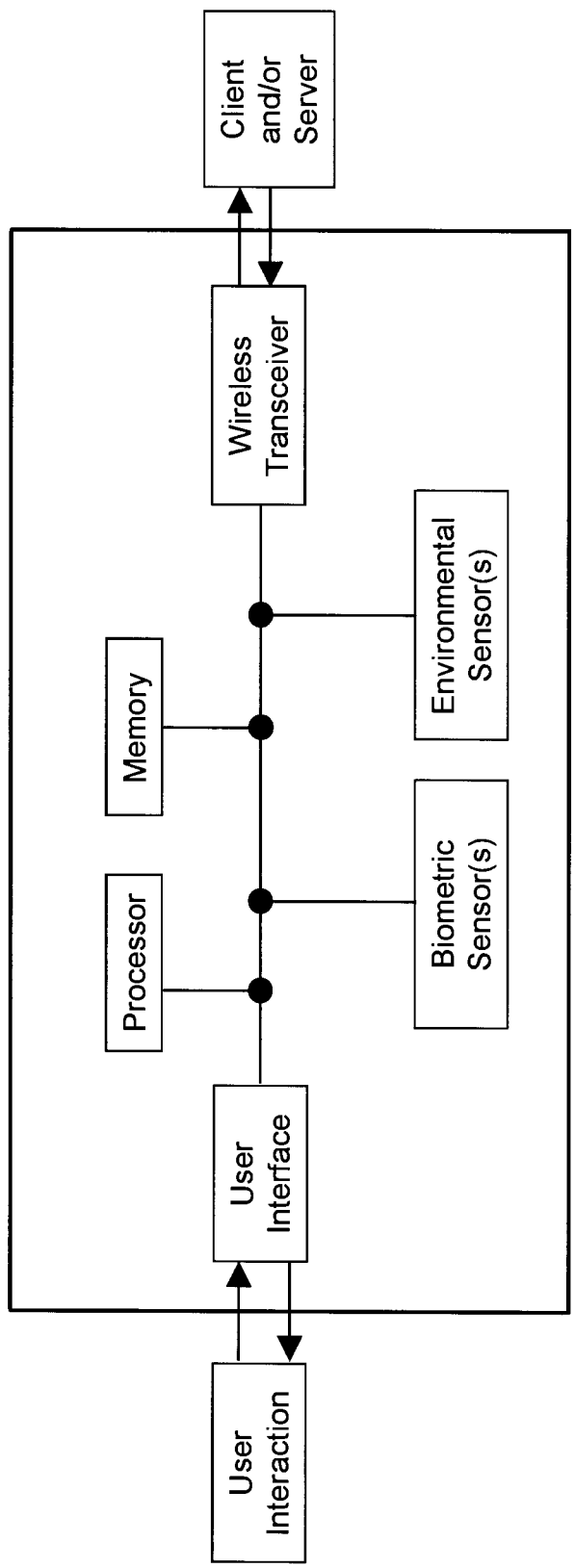
FIG. 1 illustrates an exemplary portable monitoring device which enables user interaction via a user interface, wherein the portable monitoring device may have a user interface, processor, biometric sensor(s), memory, environmental sensor(s) and/or a wireless transceiver which may communicate with an external device (for example, a client and/or server)
Figure 2:
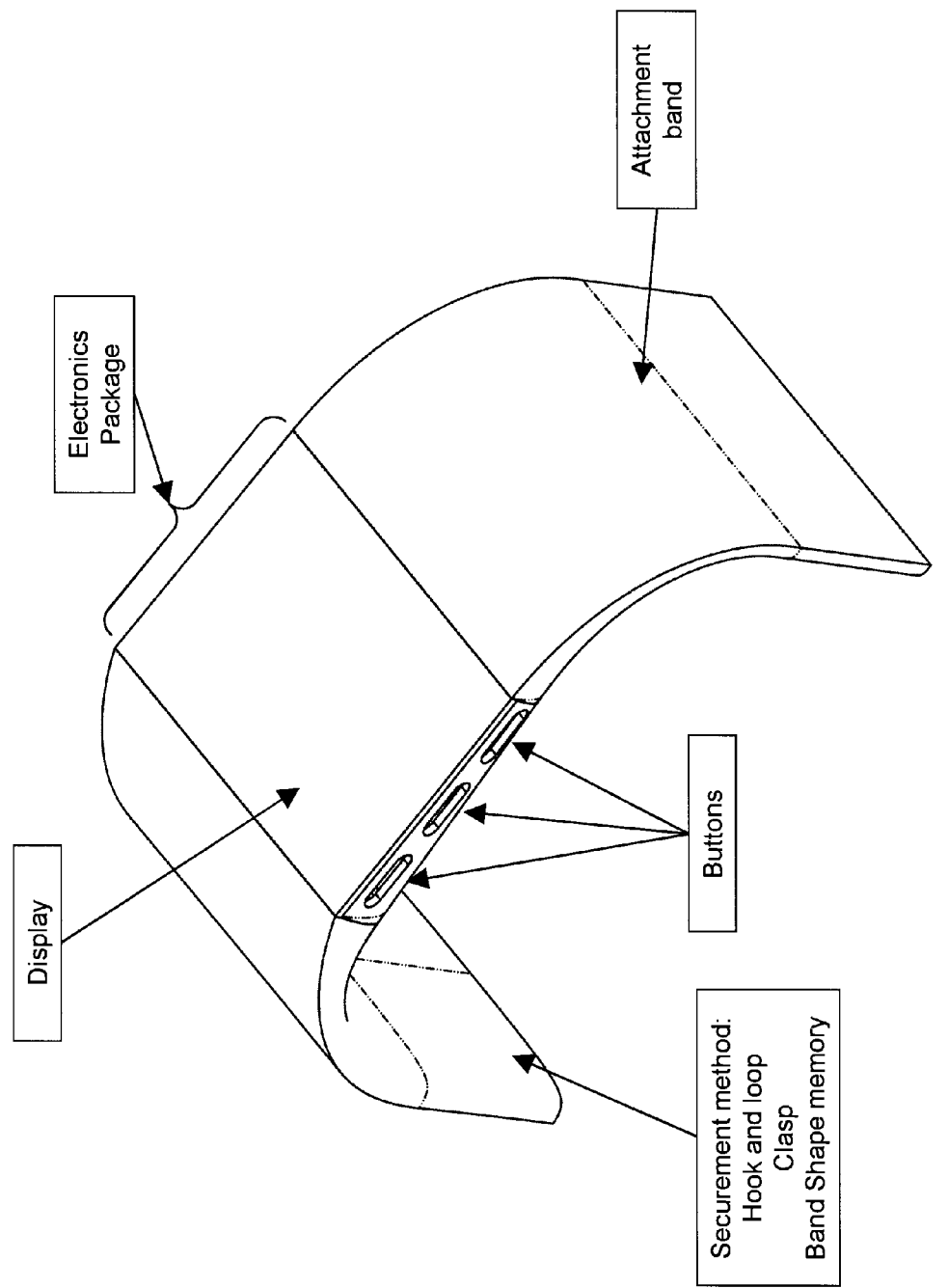
FIG. 2 illustrates an exemplary portable biometric monitoring device which may be secured to the user through the use of a band; the exemplary portable biometric monitoring device may have a display, button(s), electronics package, and/or a band or an attachment band; notably, the band or attachment band is employed to secure the portable biometric monitoring device to the user, for example, an appendage of the user, for example, via hooks and loops (e.g., Velcro), a clasp, and/or a band having memory of its shape (e.g. through the use of, for example, a spring metal band, elastic band, a "rubber" band, and/or a watch-like band)
Figure 3:
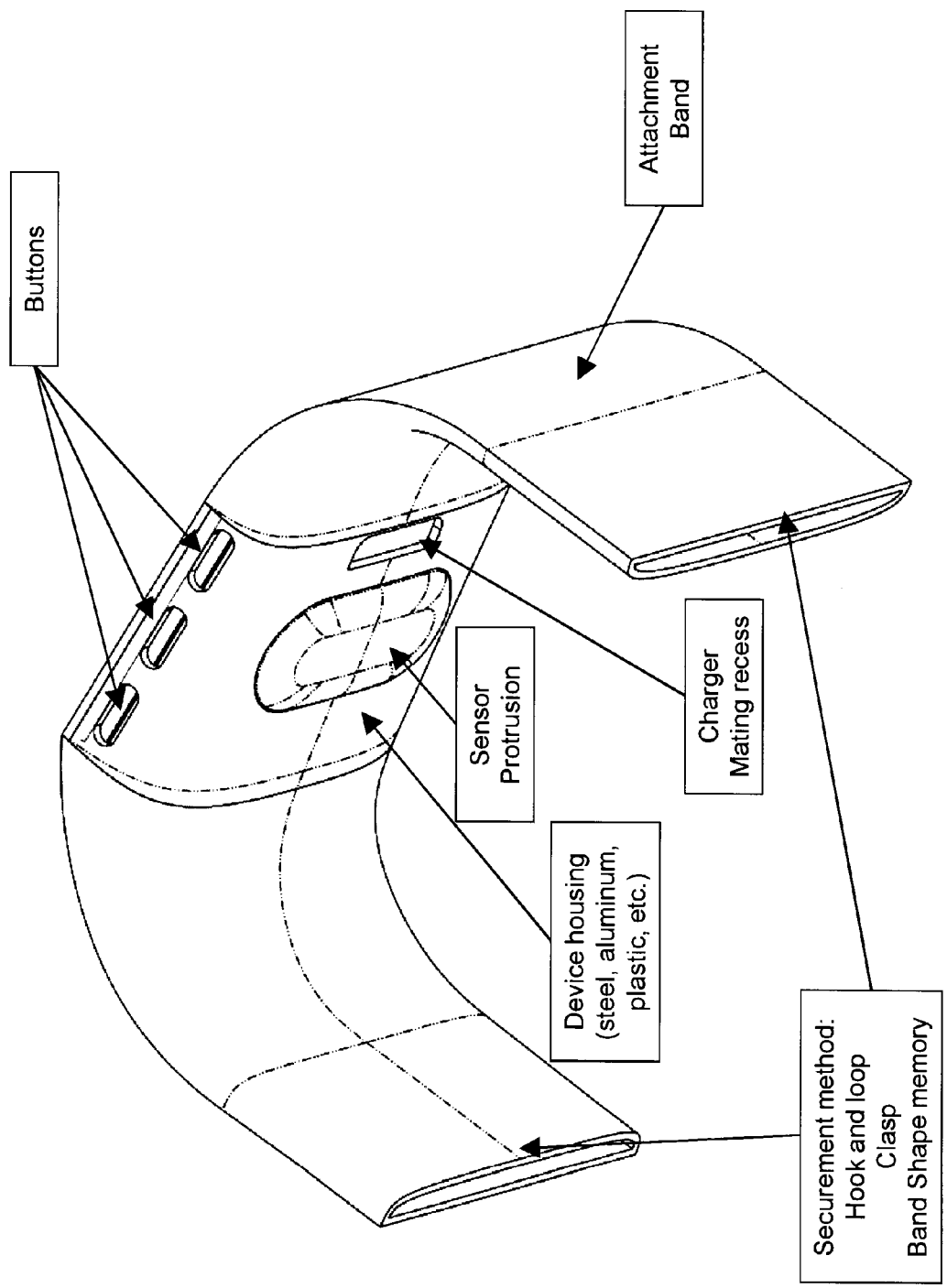
FIG. 3 illustrates a view of the skin facing portion of the portable biometric monitoring device of, for example, FIG. 2; notably, in this embodiment, the portable monitoring device includes a sensor protrusion and recess for mating a charger and/or data transmission cable; notable, the protrusion may more firmly maintain the sensor in contact with the skin of the user (for example, predetermined or fixed relational contact with the skin of the user)
Figure 4:
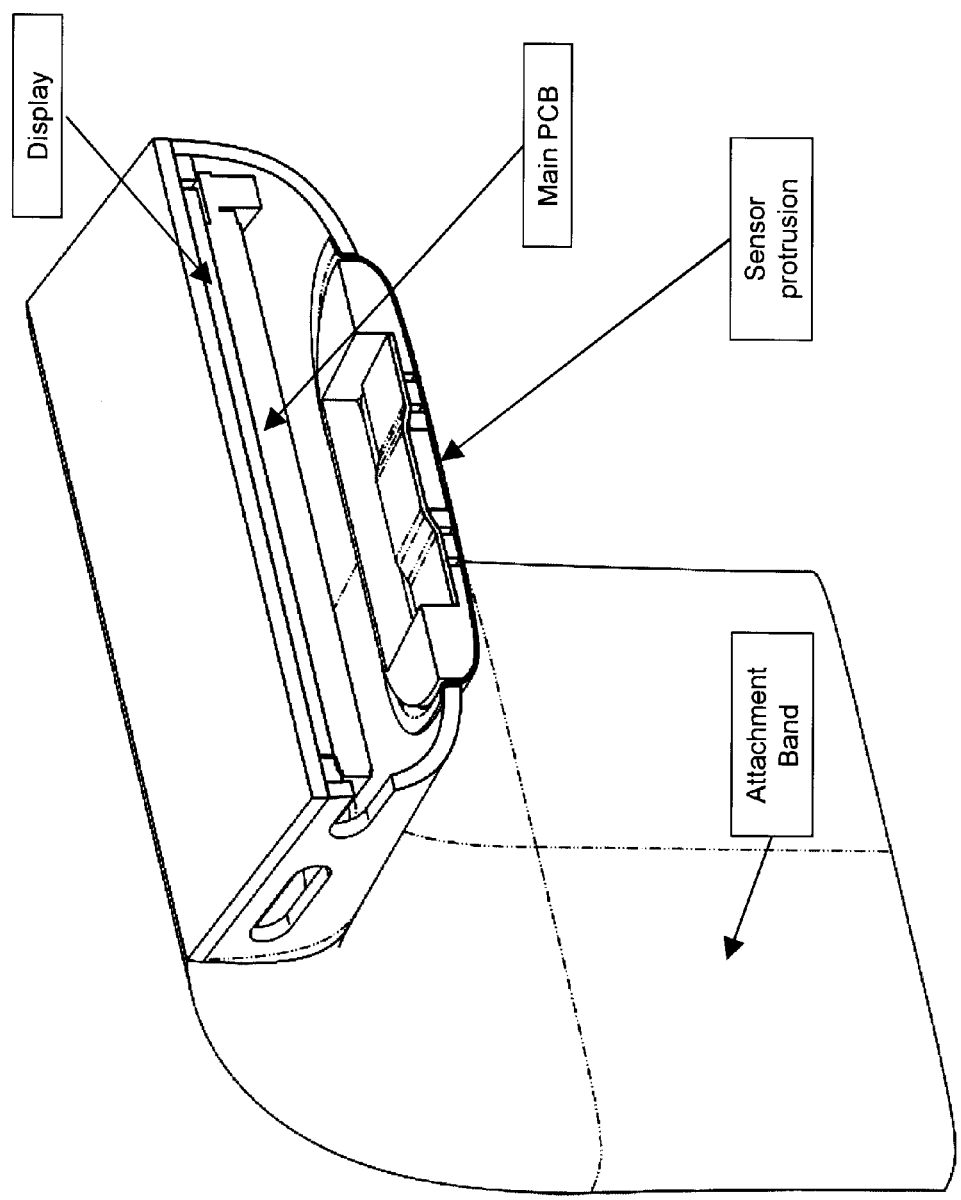
FIG. 4 illustrates a cross-sectional view (through the electronics package) of an exemplary portable biometric monitoring device.
Figure 5:
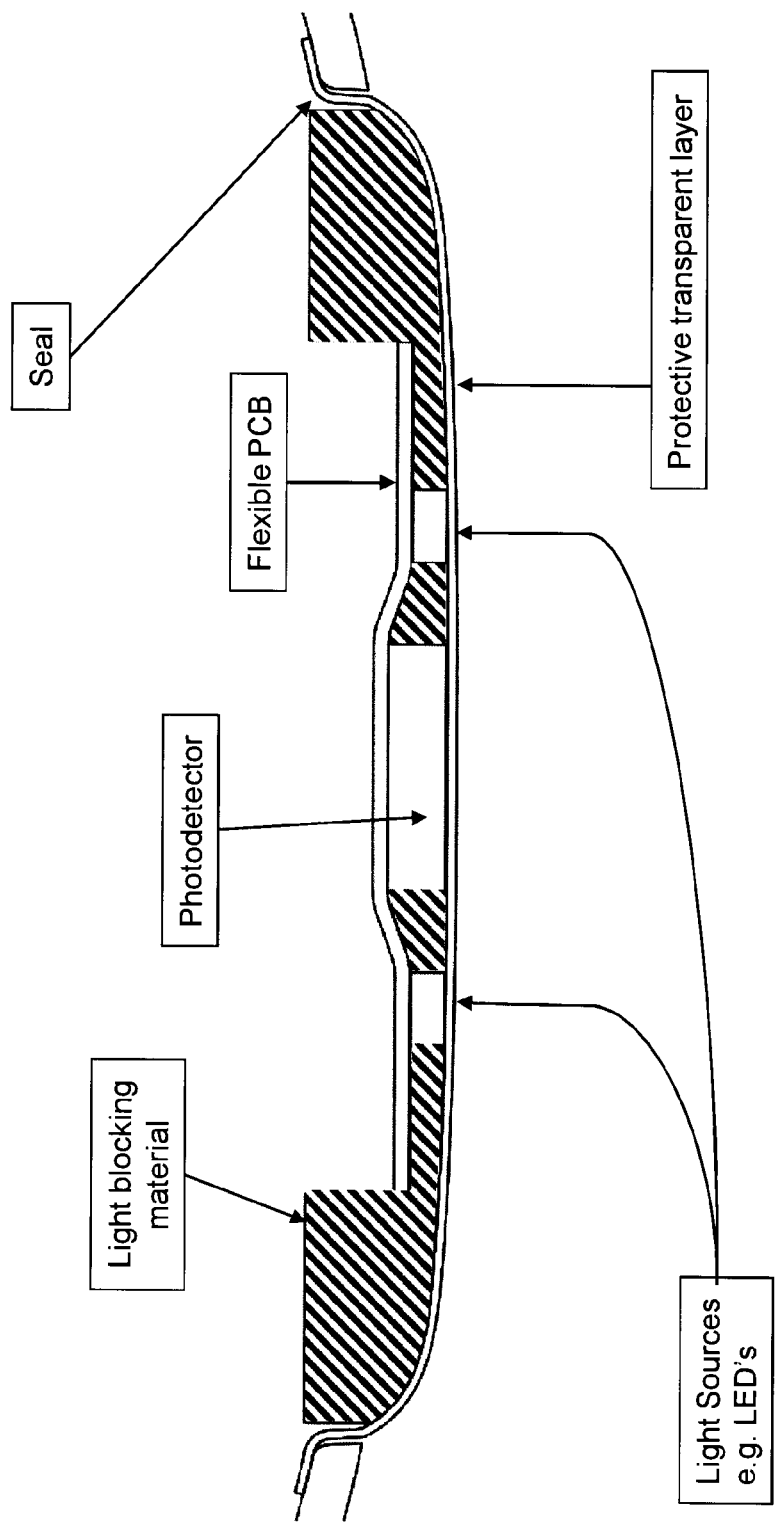
FIG. 5 illustrates a cross sectional view of a sensor protrusion of an exemplary portable biometric monitoring device; notably, two light sources (e.g. LED's) may be located on one or more sides of the photodetector (for example, either side or opposing sides of a photodetector) to enable photoplethysmography (PPG) sensing wherein light blocking material may be placed between the light sources and the photodetector to prevent any light from the light sources from going through the device body and being detected by the photodetector (in one embodiment, the light sources and photodetector are placed on a flexible PCB); a flexible transparent layer may be placed on the lower surface of the sensor protrusion to form a seal wherein the transparent layer may provide other functions such as preventing liquid from entering the device where the light sources or photodetectors are disposed or placed; notably, the transparent layer may be formed through in-mold labeling or "IML"
Figure 6:
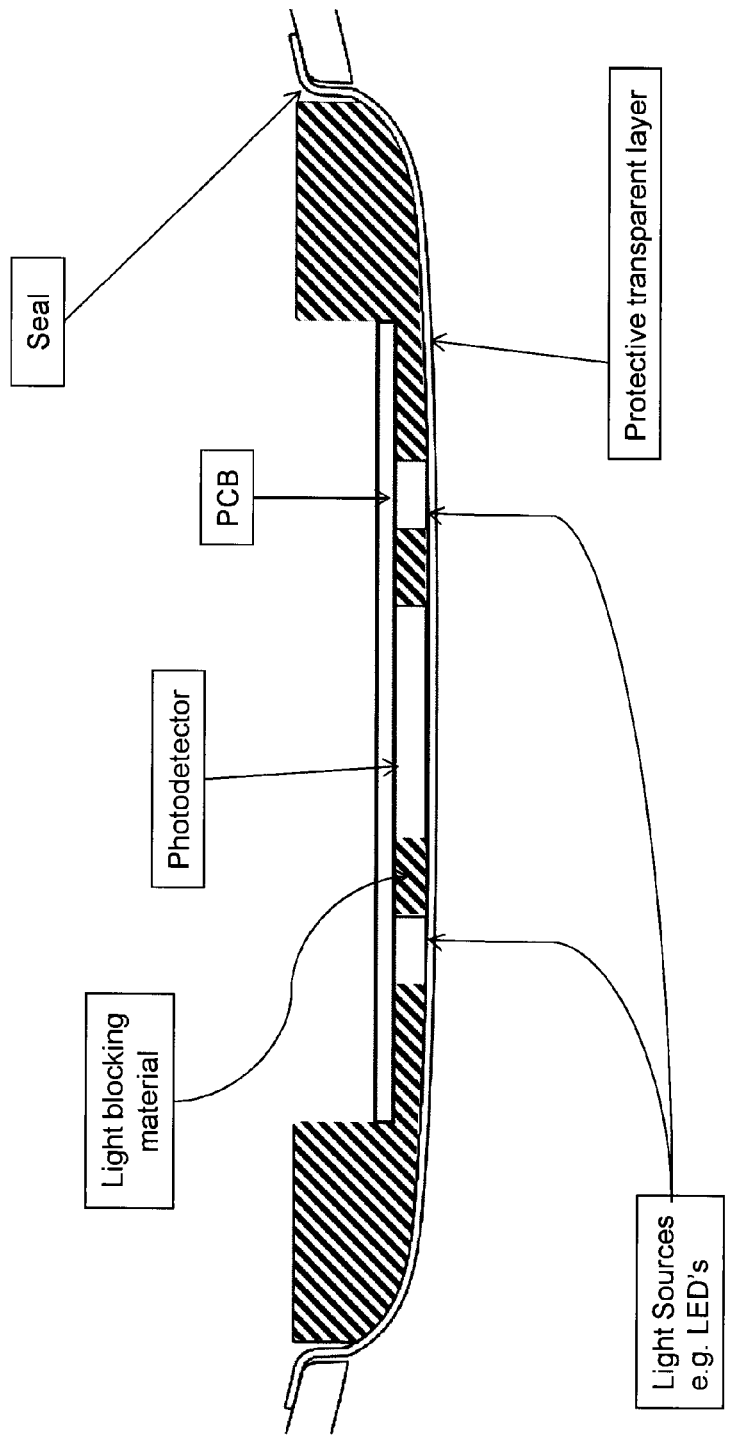
FIG. 6 illustrates a cross sectional view of a sensor protrusion of an exemplary portable biometric monitoring device; notably, the protrusion is similar to that illustrated in the exemplary portable biometric monitoring device of FIG. 5; however, the light sources and photodetector are placed on a flat and/or rigid PCB.
Figure 7:
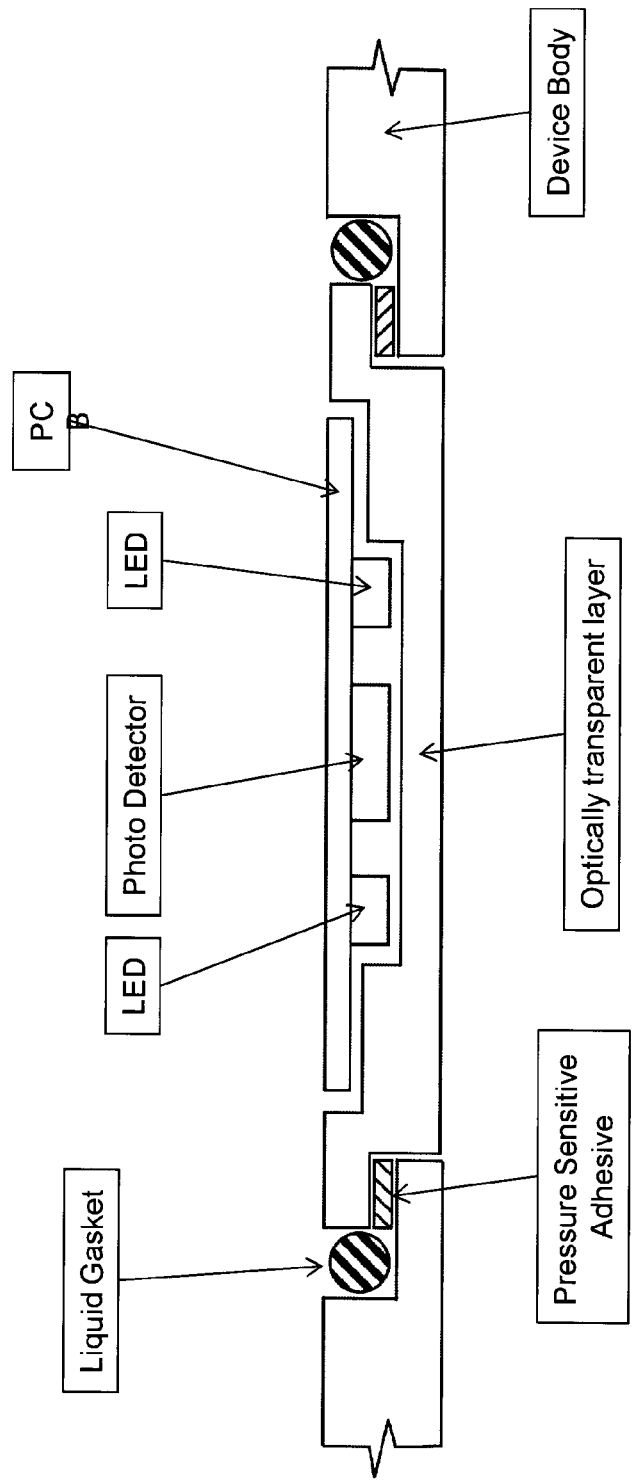
FIG. 7 illustrates another cross-sectional view of a PPG sensor, wherein in this embodiment, the PPG sensor does not include a protrusion; moreover, a gasket and/or a pressure sensitive adhesive may be employed to resist, inhibit and/or prevent liquid from entering the body of the device.

Again, there are many inventions described and illustrated herein. The present inventions are neither limited to any single aspect nor embodiment thereof, nor to any combinations and/or permutations of such aspects and/or embodiments. Each of the aspects of the present inventions, and/or embodiments thereof, may be employed alone or in combination with one or more of the other aspects of the present inventions and/or embodiments thereof. For the sake of brevity, many of those combinations and permutations are not discussed separately herein.

Moreover, many other aspects, inventions and embodiments, which may be different from and/or similar to, the aspects, inventions and embodiments illustrated in the drawings, will be apparent from the description, illustrations and claims, which follow. In addition, although various features and attributes have been illustrated in the drawings and/or are apparent in light thereof, it should be understood that such features and attributes, and advantages thereof, are not required whether in one, some or all of the embodiments of the present inventions and, indeed, need not be present in any of the embodiments of the present inventions.

DETAILED DESCRIPTION

The present inventions relate to a biometric monitoring device and methods and techniques to collect one or more types of physiological and environmental data from embedded sensors and/or external devices and communicates or relays such information to other devices or other internet-viewable sources. For example, such devices are shown in FIG. 1. While the user is wearing or manipulating the biometric monitoring device, through one or a plurality of sensors, the device may detect one or many of physiological metrics including, but not limited to, the user's heart rate.

The device may have a user interface directly on the device that indicates the state of one or more of the data types available and/or being tracked. The user interface may also be used to display data from other devices or Internet sources.

The device may implement wireless communications so that when the user and device comes within range of a wireless base station or access point, the stored data automatically uploads to an internet viewable source such as a website.

In one embodiment, the device can be a computer that executes an activity tracking application (APP). The computing device can take on any form, so long as it can process information, load and execute an application, and can communicate wirelessly with the activity tracking device. For example purposes, the device can also be or work in conjunction with a computer, a tablet computer, a smart phone, a tablet, a laptop, a desktop, a watch computer, glasses computer, or any device having access to memory and processing power.

In one embodiment, the device is configured collect motion data, activity data, and other data, such as altitude or relative altitude data, barometric pressure data, heart rate data, temperature data, alarm data, goal data, history status data, processed data, raw data, etc.

Additionally, although the computing device may usually have access to an Internet connection, every transfer between the activity tracking device and the computing device does not require Internet connection. When the computing device is connected to the Internet, the computing device can then sync data to a server. The server, in one embodiment, can be one or more distributed servers, data centers, virtualized servers in distributed data centers, etc. The server, in one embodiment, executes an activity management application that enables user account access to metrics associated with activity tracking devices.

It should be noted that there are many inventions described and illustrated herein. The inventions are neither limited to any single aspect nor embodiment thereof, nor to any combinations and/or permutations of such aspects and/or embodiments. Moreover, each of the aspects of the present inventions, and/or embodiments thereof, may be employed alone or in combination with one or more of the other aspects of the present inventions and/or embodiments thereof. For the sake of brevity, many of those permutations and combinations will not be discussed separately herein.

Further, in the course of describing and illustrating the present inventions, various circuitry, architectures, structures, components, functions and/or elements, as well as combinations and/or permutations thereof, are set forth. It should be understood that circuitry, architectures, structures, components, functions and/or elements other than those specifically described and illustrated, are contemplated and are within the scope of the present inventions, as well as combinations and/or permutations thereof.

Physiological Sensors

The biometric monitoring device of the present inventions may use one, some or all of the following sensors to acquire physiological data, including the physiological data outlined in the table below. All combinations and permutations of physiological sensors and/or physiological data are intended to fall within the scope of the present inventions. The biometric monitoring device of the present inventions may include but is not limited to the types one, some or all of sensors specified below to acquire the corresponding physiological data; indeed, other type(s) of sensors may be employed to acquire the corresponding physiological data, which are intended to fall within the scope of the present inventions. Additionally, the device may derive the physiological data from the corresponding sensor output data, but is not limited to the number or types of physiological data that it could derive from said sensor.

TABLE

| Physiological Sensors | Physiological data acquired |
| --- | --- |
| Optical Reflectometer | Heart Rate, Heart Rate Variability |
| Potential embodiments: | SpO2 (Saturation of Peripheral Oxygen) |
| Light emitter and receiver | Respiration |
| Multi or single LED and photo diode arrangement | Stress |
| | Blood pressure |
| Wavelength tuned for specific physiological signals | Arterial Stiffness |
| | Blood glucose levels |
| Synchronous detection/amplitude modulation | Blood volume |
| | Heart rate recovery |
| | Cardiac health |
| Motion Detector | Activity level detection |
| Potential embodiments: | Sitting/standing detection |
| Inertial, Gyro or Accelerometer | Fall detection |
| GPS | |
| Skin Temp | Stress |
| EMG | Muscle tension |
| EKG | Heart Rate, Heart Rate Variability, Heart Rate |
| Potential Embodiments: | Recovery |
| 1 lead | Stress |
| 2 lead | Cardiac health |
| Magnetometer | Activity level based on rotation |
| Laser Doppler | |
| Power Meter | |
| Ultra Sound | Blood flow |
| Audio | Heart Rate, Heart Rate Variability, Heart Rate Recovery |
| | Laugh detection |
| | Respiration |
| | Respiration type-snoring, breathing, breathing problems |
| | User's voice |
| Strain gauge | Heart Rate, Heart Rate Variability |
| Potential embodiment: | Stress |
| In a wrist band | |
| Wet sensor | Stress |
| Potential embodiment: | Swimming detection |
| galvanic skin response | Shower detection |

In one exemplary embodiment, the biometric monitoring device includes an optical sensor to detect, sense, sample and/or generate data that may be used to determine information representative of, for example, stress (or level thereof), blood pressure and/or heart rate of a user. (See, for example, FIGS. 2-7 and 17-23).

In this embodiment, the biometric monitoring device includes an optical sensor having one or more light sources (LED, laser, etc.) to emit or output light into the user's body and/or light detectors (photodiodes, phototransistors, etc.) to sample, measure and/or detect a response or reflection and provide data used to determine data which is representative of stress (or level thereof), blood pressure and/or heart rate of a user (e.g., using photoplethysmography).

Figure 15:
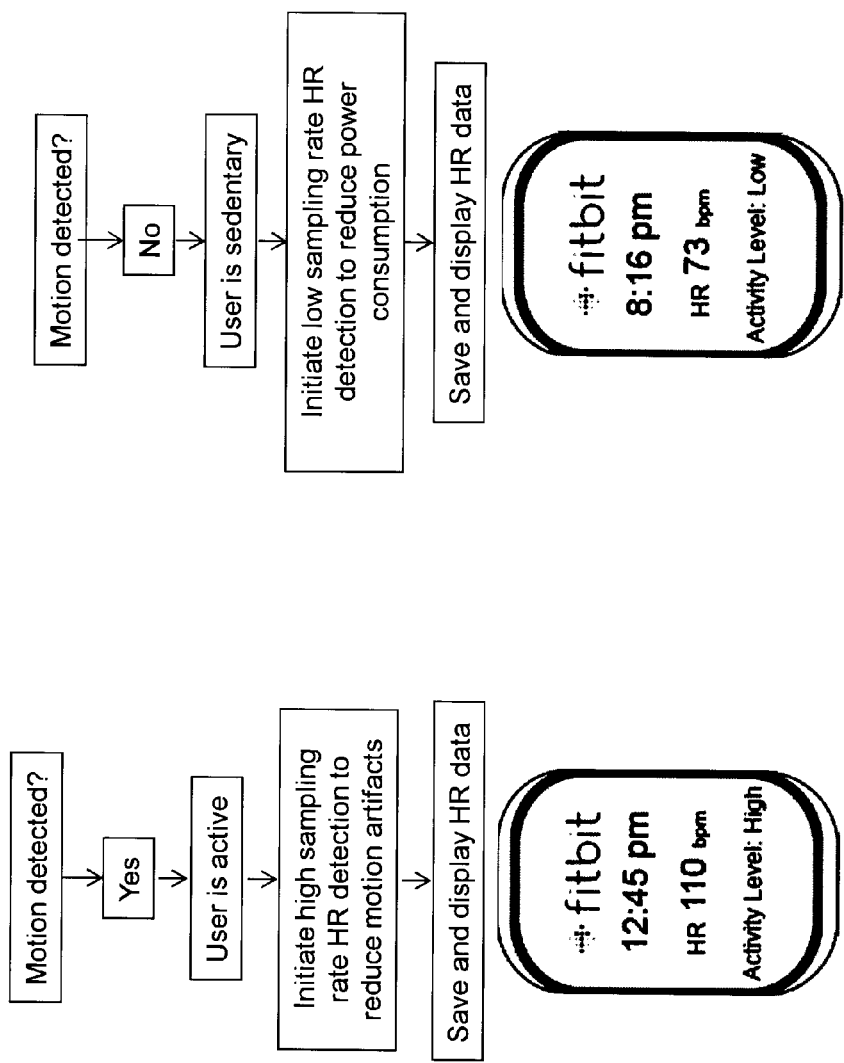
FIG. 15 illustrates, in a flow diagram form, the operation of a portable biometric monitoring device which changes how the device detects a user's heart rate based on how much movement the device is experiencing; in this embodiment, there is motion detected (e.g. through the use of an accelerometer), the user may be considered active and high sampling rate heart rate detection may occur to reduce motion artifacts in the heart rate measurement; the data may be saved and/or displayed; notably, where the user is not moving, low sampling heart rate detection (which does not consume as much power) may be adequate to measure a heart rate.
Figure 24:
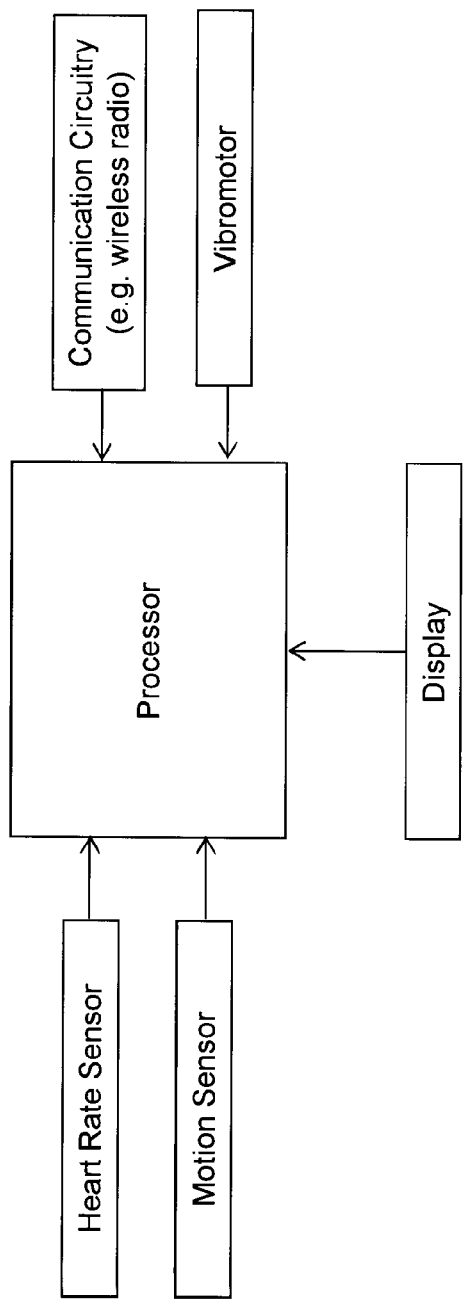
FIG. 24 illustrates certain circuitry/elements of an exemplary portable biometric monitoring device having a heart rate or PPG sensor, motion sensor, display, vibromotor/vibramotor, and communication circuitry which are connected to a processor.
Figure 25:
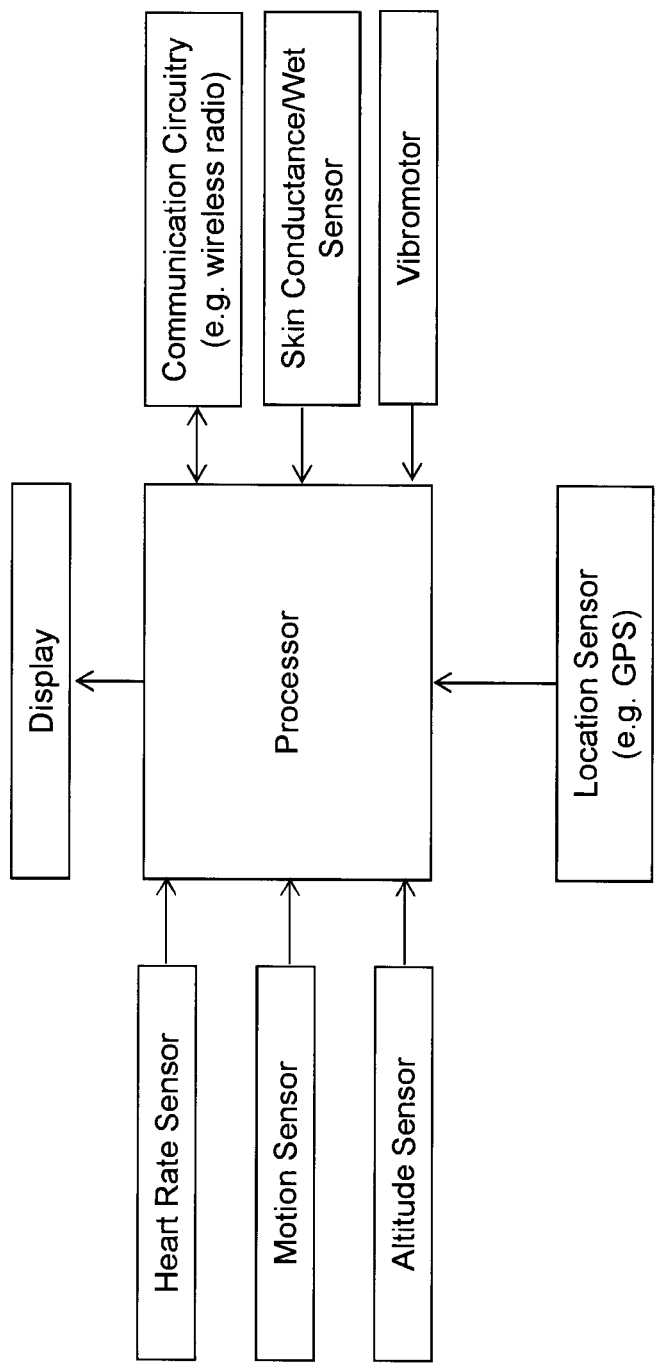
FIG. 25 illustrates certain circuitry/elements of an exemplary portable biometric monitoring device having a heart rate or PPG sensor, motion sensor, display, vibromotor/vibramotor, location sensor, altitude sensor, skin conductance/wet sensor and communication circuitry which is connected to a processor.

In one exemplary embodiment, a user's heart rate measurement may be triggered by criteria determined by one or more sensors (or processing circuitry connected to them). For instance, when data from the motion sensor(s) indicates a period of stillness or little motion, the biometric monitoring device may trigger, acquire and/or obtain a heart rate measurement or data. (See, for example, FIGS. 15, 24 and 25). In one embodiment, when the motion sensor(s) indicate user activity or motion (for example, motion that is not suitable or optimum to trigger, acquire and/or obtain desired heart rate measurement or data (for example, data used to determine a user's resting heart rate), the biometric monitoring device and/or the sensor(s) employed to acquire and/or obtain desired heart rate measurement or data may be placed or remain in a low power state. (Note that measurements taken during motion may be less reliable and may be corrupted by motion artifact.)

In another embodiment, the biometric monitoring device of the present inventions may employ data indicative of user activity or motion (for example, from one or more motion sensors) adjust or modify characteristics of triggering, acquiring and/or obtaining desired heart rate measurement or data (for example, to improve robustness to motion artifact). For instance, data indicative of user activity or motion may adjust or modify the sampling rate and/or resolution mode of sensors which acquire heart rate data (for example, where the amount of user motion exceeds a certain threshold, the biometric monitoring device may increase the sampling rate and/or increase the sampling resolution mode of sensors employed to acquire heart rate measurement or data. Moreover, the biometric monitoring device may adjust or modify the sampling rate and/or resolution mode of the motion sensor(s) during such periods of user activity or motion (for example, periods where the amount of user motion exceeds a certain threshold). In this way, when the biometric monitoring device determines or detects such user activity or motion, the motion sensor(s) may be placed into a higher sampling rate and/or higher sampling resolution mode to, for example, enable more accurate adaptive filtering on the heart rate signal. (See, for example, FIG. 15).

Notably, where the biometric monitoring device employs optical techniques to acquire heart rate measurements or data (e.g., photoplethysmography), a motion signal may be employed to determine or establish a particular approach or technique to data acquisition or measurement (e.g., synchronous detection rather than a non-amplitude modulated approach) and/or analysis thereof. (See, for example, FIG. 21). In this way, the data which is indicative of the amount of user motion or activity establishes or adjusts the type or technique of data acquisition or measurement by the optical heart rate data acquisition sensors.

For example, in one preferred embodiment, the biometric monitoring device and technique of the present inventions may adjust and/or reduce the sampling rate of optical heart rate sampling when the motion detector circuitry detects or determines that the user's motion is below a threshold (for example, the biometric monitoring device determines the user is sedentary or asleep). (See, for example, FIG. 15). In this way, the biometric monitoring device may control its power consumption (for example, reduce power consumption by reducing the sampling rate—for instance, the biometric monitoring device may sample the heart rate (via the heart rate sensor) once every 10 minutes, or 10 seconds out of every 1 minute. Notably, the biometric monitoring device may, in addition thereto or in lieu thereof, control power consumption via controlling data processing circuitry analysis and/or data analysis techniques in accordance with motion detection. As such, the motion of the user may impact the heart rate data acquisition parameters and/or data analysis or processing thereof.

In yet another embodiment, the biometric monitoring device may employ the sensors to calculate heart rate variability when the device determines the user to be sedentary or asleep. Here, the device may operate the sensors in a higher-rate sampling mode (relative to non-sedentary periods or periods of user activity that exceed a predetermined threshold) to calculate heart rate variability. The biometric monitoring device (or external device) may employ heart rate variability as an indicator of cardiac health or stress.

Indeed, in a preferred embodiment, the biometric monitoring device measures and/or determines the user's stress level and/or cardiac health when the user is sedentary and/or asleep (for example, as detected and/or determined by the biometric monitoring device). The biometric monitoring device of the present inventions may determine the user's stress level, health state (e.g., risk, onset, or progression of fever or cold) and/or cardiac health using sensor data which is indicative of the heart rate variability, galvanic skin response, skin temperature, body temperature and/or heart rate. In this way, processing circuitry of the biometric monitoring device may determine and/or track the user's "baseline" stress levels over time and/or cardiac "health" over time. In another embodiment, the device measures a physiologic parameter of the user during one or more periods where the user is motionless (or the user's motion is below a predetermined threshold), sitting, lying down, asleep, or in a particular sleep stage (e.g., deep sleep). Such data may also be employed as a "baseline" for stress-related parameters, health-related parameters (e.g., risk or onset of fever or cold), cardiac health, heart rate variability, galvanic skin response, skin temperature, body temperature and/or heart rate.

Notably, in one embodiment, the biometric monitoring device may automatically detect or determine when the user is attempting to go to sleep, entering sleep, is asleep and/or is awoken from a period of sleep. In this embodiment, the biometric monitoring device may employ physiological sensors to acquire data wherein the data processing circuitry correlates a combination of heart rate, heart rate variability, respiration rate, galvanic skin response, motion, and/or skin and/or body temperature sensing to detect or determine if the user is attempting to go to sleep, entering sleep, is asleep and/or is awoken from a period of sleep. In response, the biometric monitoring device may, for example, acquire physiological data (of the type and in the manner as described herein) and/or determine physiological conditions of the user (of the type and in the manner as described herein). For example, a decrease or cessation of user motion combined with a reduction in user heart rate and/or a change in heart rate variability may indicate that the user has fallen asleep. Subsequent changes in heart rate variability and galvanic skin response may be used to determine transitions of the user's sleep state between two or more stages of sleep (for example, into lighter and/or deeper stages of sleep). Motion by the user and/or an elevated heart rate and/or a change in heart rate variability may be used to determine that the user has awoken.

In an embodiment, the biometric monitoring device is one component of a system for monitoring sleep, where the system comprises a secondary device capable of communicating with the biometric monitoring device and adapted to be placed near the sleeper (e.g., an alarm clock). The secondary device may have a shape and mechanical and/or magnetic interface to accept the biometric monitoring device for safe keeping, communication, and/or charging. Notably, the communication between the biometric monitoring device and the secondary device may be provided through wireless communication techniques/methods and protocols such as Bluetooth, Bluetooth 4.0, RFID, NFC, or WLAN. The secondary device may comprise sensors to assist in sleep or environmental monitoring such as, for example, sensors that measure ambient light, noise and/or sound (e.g., to detect snoring), temperature, humidity, and air quality (pollen, dust, CO2, etc). In an embodiment, the secondary device may communicate with an external service such as www.fitbit.com or server (e.g., personal computer). Communication may be achieved through wired (e.g., Ethernet, USB) or wireless (e.g., WLAN, Bluetooth, RFID, NFC, cellular) circuitry and protocols to transfer data to and/or from the secondary device. The secondary device may also act as a relay to transfer data to and/or from the biometric monitoring device to an external service such as www.fitbit.com or other service (e.g., news, social network updates, email, calendar notifications), or server (e.g., personal computer, mobile phone, tablet). Calculation of the user's sleep data may be executed on one or both devices or an external service (e.g., a cloud server) using data from one or both devices.

The secondary device may be equipped with a display to display data obtained by the secondary device or data transferred to it by the biometric monitoring device, the external service, or a combination of data from the biometric monitoring device, the secondary device, and/or the external service. For example, the secondary device may display data indicative of the user's heart rate, total steps for the day, activity and/or sleep goal achievement, the day's weather (measured by the secondary device or reported for a location by an external service), etc. In another example, the secondary device may display data related to the ranking of the user relative to other users, such as total weekly step count. In yet another embodiment, the biometric monitoring device may be equipped with a display to display data obtained by the biometric monitoring device, the secondary device, the external service, or a combination of the three sources. In embodiments where the first device is equipped with a wakeup alarm (e.g., vibramotor, speaker), the secondary device may act as a backup alarm (e.g., using an audio speaker). The secondary device may also have an interface (e.g., display and buttons or touch screen) to create, delete, modify, or enable alarms on the first and/or the secondary device.

In another embodiment, the biometric monitoring device may automatically detect or determine whether it is or is not attached to, disposed on and/or being worn by the user. In response to detecting or determining the biometric monitoring device is not attached to, disposed on and/or being worn by the user, the biometric monitoring device (or selected portions thereof) may implement or be placed in a low power mode of operation—for example, the optical heart rate sensor and/or circuitry may be placed in a lower power or sleep mode). For example, in one embodiment, the biometric monitoring device includes one or more light detectors (photodiodes, phototransistors, etc) wherein, if at a given light intensity setting, one or more light detectors provides a low return signal, the biometric monitoring device may interpret the data is indicative of the device not being worn. Upon such a determination, the device may reduce its power consumption—for example, "disable" or adjust the operating conditions of the stress and/or heart rate detection sensors and/or circuitry (for example, reduce duty cycle of or disable the light source(s) and/or detector(s), and/or disable or attenuate associated circuitry or portions thereof). In addition, the biometric monitoring device may periodically determine (e.g., once per second) if the operating conditions of the stress and/or heart rate detection sensors and/or associated circuitry should be restored to a normal operating condition (for example, light source(s), detector(s) and/or associated circuitry should return to a normal operating mode for heart rate detection). In another embodiment, the biometric monitoring device restores the operating conditions of the stress and/or heart rate detection sensors and/or associated circuitry upon detection of a triggerable event—for example, upon detecting motion of the device (for example, based on data from one or more motion sensor(s)) and/or detecting a user input via the user interface (for example, a tap, bump or swipe). In a related embodiment, the biometric monitoring device may, for power saving purposes, reduce its rate of heart rate measurement collection to, for instance, one measurement per minute whilst the user is not highly active and the user may put the device into a mode of operation to generate measurements on demand or at a faster rate (e.g., once per second), for instance, by pushing a button.

Figure 11:
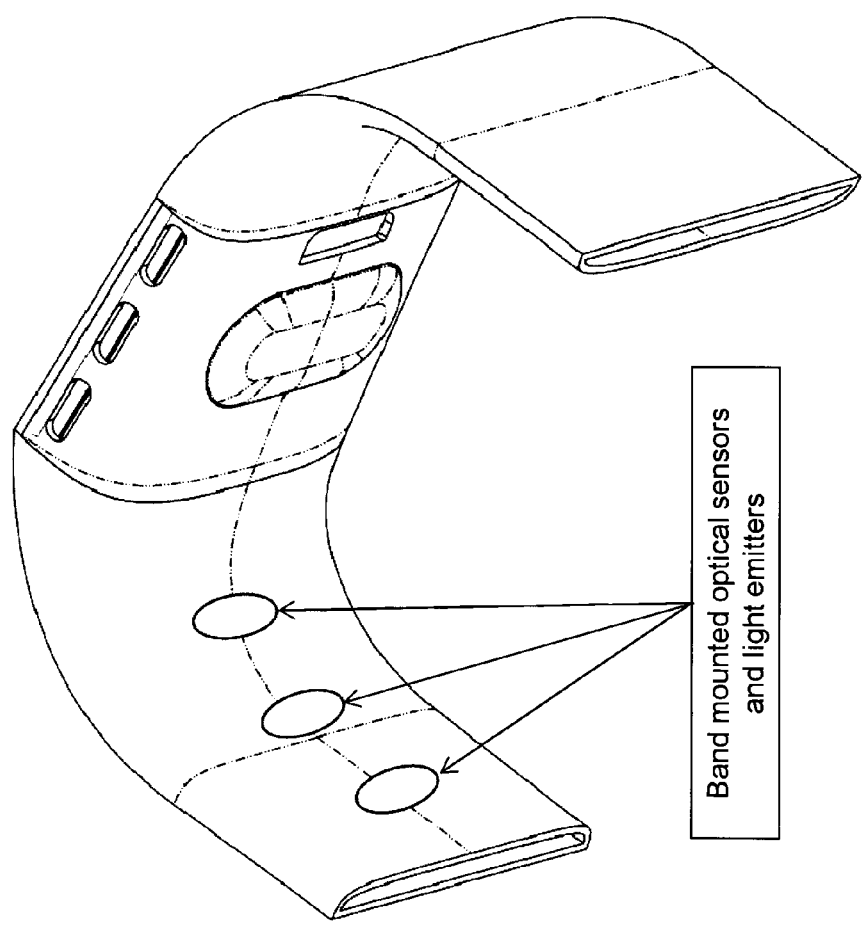
FIG. 11 illustrates an exemplary portable biometric monitoring device having a band and optical sensors and light emitters disposed therein.
Figure 12:
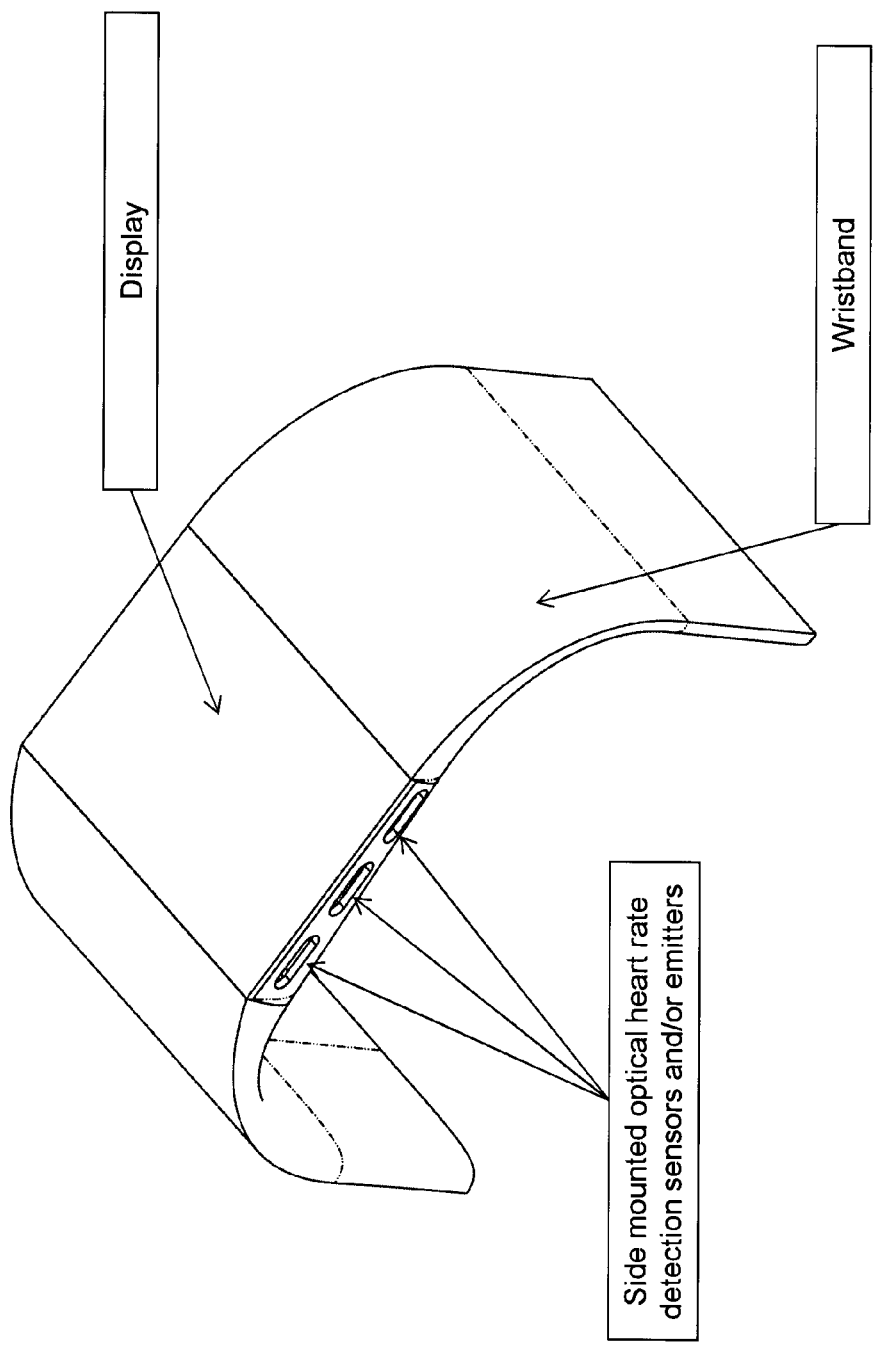
FIG. 12 illustrates a portable biometric monitoring device having a display and wristband; an optical PPG (e.g. heart rate) detection sensors and/or emitters may be disposed or located on the side of the device; notably, in one embodiment, the sensors and/or emitters are disposed or located in buttons mounted on the side of the device.
Figure 13:
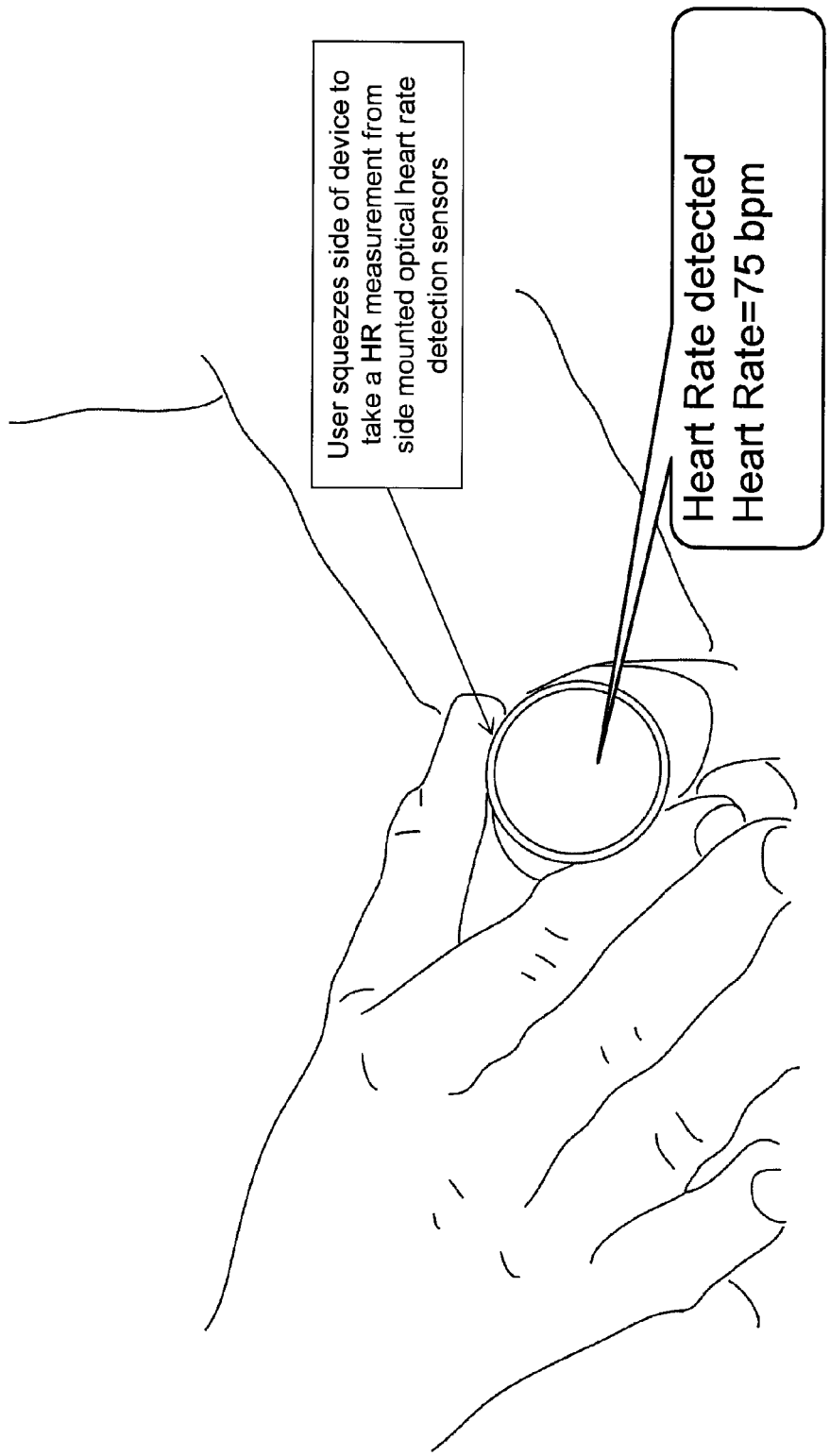
FIG. 13 illustrates a user who is inputting a user input by pressing the side of a portable biometric monitoring device wherein, in response, the device takes a heart rate measurement from a side mounted optical heart rate detection sensor; a display of the device may thereafter display whether or not the heart rate has been detected and/or display the user's heart rate.

In one embodiment, the optical sensors (sources and/or detectors) may be disposed on an interior or skin side of the biometric monitoring device (i.e., a side whereby the surface of the device contacts, touches and/or faces the skin of the user (hereinafter "skin side"). (See, for example, FIGS. 2-7). In another embodiment, the optical sensors may be disposed on one or more sides of the device, including the skin side and one or more sides of the device that face or are exposed to the ambient environment (environmental side). (See, for example, FIGS. 11-13). Notably, the data from such optical sensors may be representative of physiological data and/or environmental data. Indeed, in one embodiment, the optical sensors provide, acquire and/or detect information from multiple sides of the biometric monitoring device whether or not the sensors are disposed on one or more of the multiple sides. For example, the optical sensors may obtain data related to the ambient light conditions of the environment.

Where optical sensors are disposed or arranged on the skin side of the biometric monitoring device, in operation, a light source emits light upon the skin of the user and, in response, a light detector samples, acquires and/or detects a response or reflected light from the skin (and from inside the body). The one or more sources and detectors may be arranged in an array or pattern that enhances or optimizes the SNR and/or reduces or minimizes power consumption by light sources and detectors. These optical detectors sample, acquire and/or detect physiological data which may then be processed or analyzed (for example, by resident processing circuitry) to obtain data which is representative of, for example, a user's heart rate, respiration, heart rate variability, oxygen saturation (SpO2), blood volume, blood glucose, skin moisture and skin pigmentation level.

The source(s) may emit light having one or more wavelengths which are specific or directed to a type of physiological data to be collected. The optical detectors may sample, measure and/or detect one or more wavelengths that are also specific or directed to a type of physiological data to be collected and physiological parameter (of the user) to be assessed or determined. For instance, in one embodiment, a light source emitting light having a wavelength in the green spectrum (for example, an LED that emits light having wavelengths corresponding to the green spectrum) and photodiode positioned to sample, measure and/or detect a response or reflection may provide data used to determine or detect heart rate. In contrast, a light source emitting light having a wavelength in the red spectrum (for example, an LED that emits light having wavelengths corresponding to the red spectrum) and a light source emitting light having a wavelength in the infrared spectrum (for example, an LED that emits light having wavelengths corresponding to the IR spectrum) and photodiode positioned to sample, measure and/or detect a response or reflection may provide data used to determine or detect SpO2.

Indeed, in one embodiment, the color or wavelength of the light emitted by the LED (or set of LEDs) may be modified, adjusted and/or controlled in accordance with a predetermined type of physiological data being acquired or conditions of operation. Here, the wavelength of the light emitted by the LED is adjusted and/or controlled to optimize and/or enhance the "quality" of the physiological data obtained and/or sampled by the detector. For example, the color of the light emitted by the LED may be switched from infrared to green when the user's skin temperature or the ambient temperature is cool in order to enhance the signal corresponding to cardiac activity. (See, for example, FIG. 20).

The biometric monitoring device, in one embodiment, includes a window (for example, a visually opaque window) in the housing to facilitate optical transmission between the optical sensors and the user. Here, the window may permit light (for example, of a selected wavelength) to be emitted by, for example, one or more LEDs, onto the skin of the user and a response or reflection to pass into the housing to be sampled, measured and/or detected by, for example, one or more photodiodes. In one embodiment, the circuitry related to emitting and receiving light may be disposed in the interior of the device housing and underneath a plastic or glass layer (for example, painted with infrared ink) or an infrared lens which permits infrared light to pass but not light in the human visual spectrum. In this way, the light transmission is invisible to the human eye.

Figure 8:
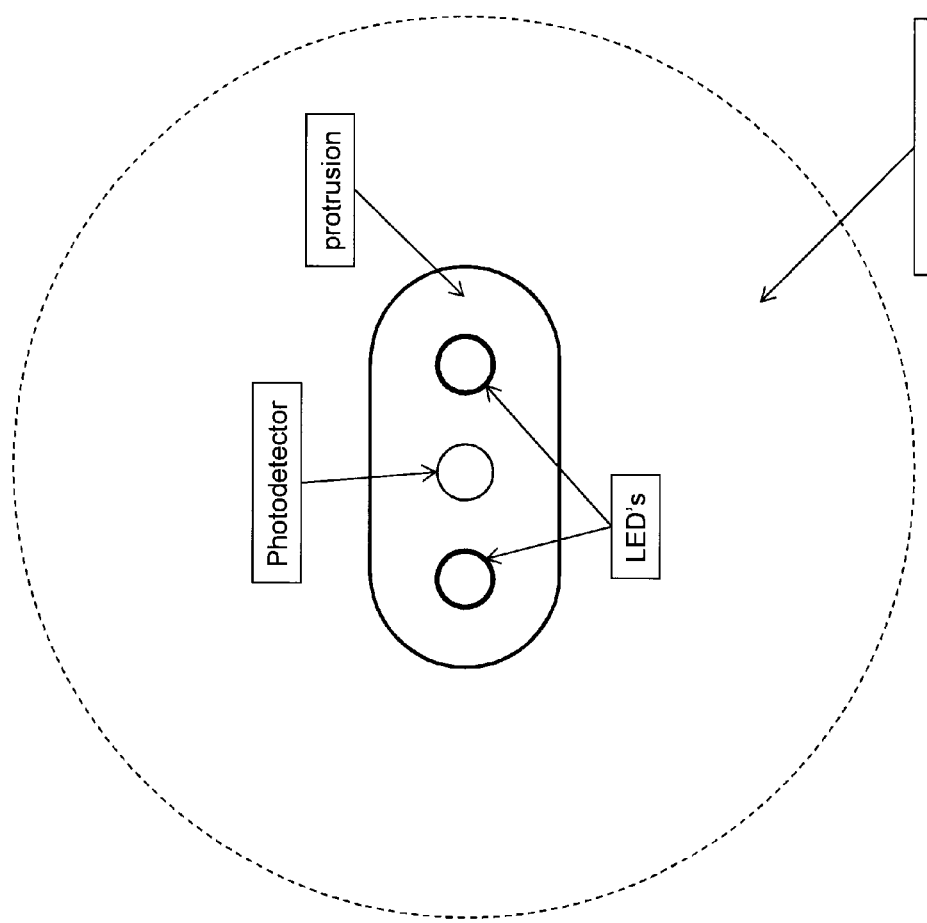
FIG. 8 illustrates an exemplary geometry of a PPG light source and photodetector wherein, in this embodiment, two light sources are placed on either side of a photodetector; notably, the lights sources and photodetector may be disposed or located in a protrusion on the back of a portable biometric monitoring device which may also operate as a smart watch (the side which faces the skin of the user)
Figure 9:
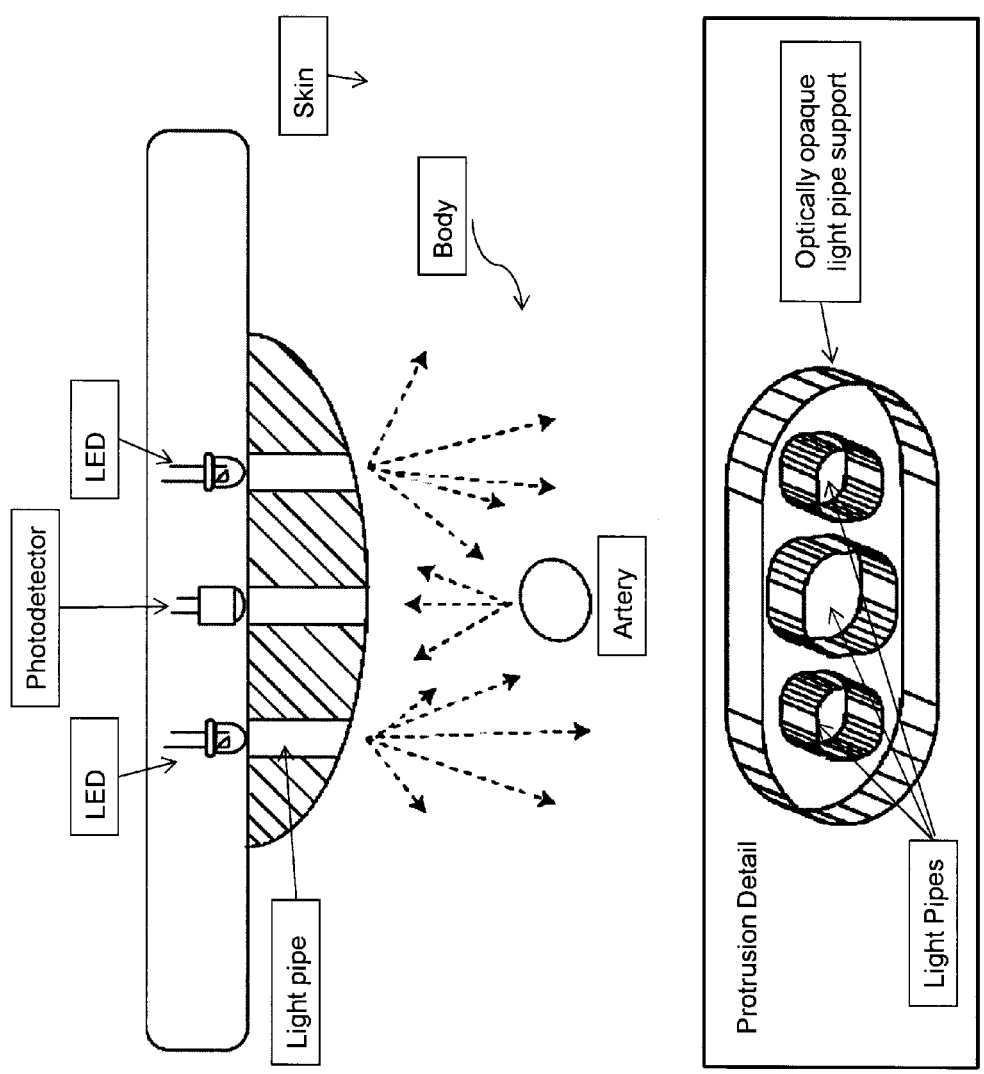
FIG. 9 illustrates an exemplary PPG sensor having a photodetector and two LED light sources which may be disposed or located in a portable biometric monitoring device having a protrusion; notably, in this embodiment, light pipes are optically connected the LED's and photodetector to the surface of the user's skin, wherein, in operation, the light from the light sources scatters/reflects off of blood in the body, some of which reaches the photodetector via the light pipes; notably, the light pipes preferentially direct or transmit light along a predetermined path, for example, defined by the geometry and/or material of the light pipe.
Figure 10:
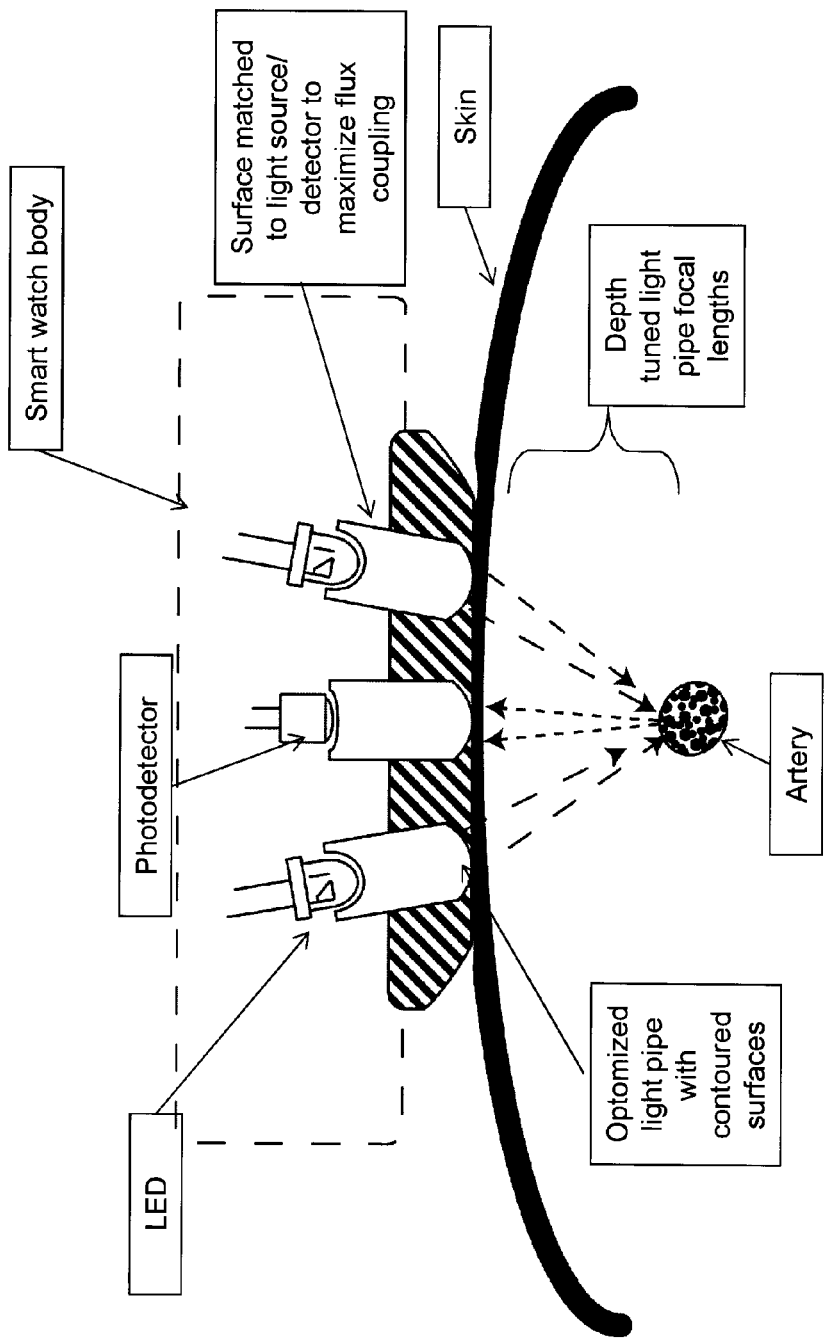
FIG. 10 illustrates an exemplary PPG detector having a protrusion with curved sides to reduce and/or minimize any discomfort to the user during operation and/or to more firmly maintain the sensor in contact with the skin of the user (for example, predetermined or fixed relational contact with the skin of the user); in this embodiment, the surface of light pipes are connect the photodetector and LEDs to the user's skin and are contoured to enhance and/or maximize light flux coupling between the LEDs and photodetectors to the light pipes; notably, the end of the light pipes which face the user's skin may also contoured wherein this contour may provide focusing or defocusing to enhance and/or optimize the PPG signal (for example, the contour may focus light to a certain depth and location which coincides with an area where blood flow is likely to occur); in addition, the vertex of these foci overlap or are very close together so that the photodetector may receive, for example, the maximum possible amount of scattered/reflected light.

The biometric monitoring device may employ light pipes or other light transmissive structures. (See, for example, FIGS. 8-10). In this regard, in one embodiment, light is directed from the light source to the skin of the user through light pipes or other light transmissive structures. Scattered light from the user's body may be directed back to the optical circuitry through the same or similar structures. Indeed, the transmissive structures may employ a material and/or optical design to facilitate low light loss (for example, a lens) thereby improving SNR of the photo detector and/or reduce power consumption of the light source(s) (light emitters and/or light detectors). In one embodiment, the light pipes or other light transmissive structures may include a material that selectively transmits light having one or more specific or predetermined wavelengths with higher efficiency than others, thereby acting as a bandpass filter. This bandpass filter may be tuned to improve the signal of a specific physiological data type. For example, in one embodiment, an In-Mold-Labeling or "IML" light transmissive structure may be implemented wherein the structure uses a material with predetermined or desired optical characteristics to create a specific bandpass characteristic, for example, to pass infrared light with greater efficiency than light of other wavelengths (for example, light having a wavelength in human visible spectrum). In another embodiment, a biometric monitoring device may employ light transmissive structure having an optically opaque portion (including certain optical properties) and an optically transparent portion (including optical properties different from the optically opaque portion). Such a structure may be provided via a double-shot or two step molding process wherein optically opaque material is injected and optically transparent material is injected. A biometric monitoring device implementing such a light transmissive structure may include different transmissive property for different wavelengths depending on the direction of light travel through the structure. For example, in one embodiment, the optically opaque material may include a property of being reflective to a specific wavelength range so as to more efficiently transport light from the light emitter(s) and from the user's body back to the skin detector (which may be of a different wavelength(s) relative to the wavelength(s) of the emitted light).

In another embodiment which implements light transmissive structures (for example, structures created or formed through IML), such structures may include a mask consisting of an opaque material which limits the aperture of one, some or all of the light source(s) and/or detector(s). In this way, the light transmissive structures selectively "define" a preferential volume of the body that light is emitted into and/or detected from. Notably, other mask configurations may be employed or implemented in connection with the inventions described and/or illustrated herein; all such mask configurations to, for example, improve the photoplethysmography signal, and which are implemented in connection with the inventions described and/or illustrated herein, are intended to fall within the scope of the present inventions.

In any of the light transmissive structures described herein, the surface of the optics or device body may include a hard coat paint, hard coat dip, or optical coatings (such as anti-reflection), scratch resistance, anti-fog, and/or wavelength band block (such as ultraviolet light blocking). Such characteristics or materials may improve the operation, accuracy and/or longevity of the biometric monitoring device.

In one embodiment, the biometric monitoring device includes a concave or convex shape, on the skin side of the device, to focus light towards a specific volume at a specific depth in the skin and increase the efficiency of light collected from that point into the photodetector. (See, for example, FIGS. 8-10). Where such a biometric monitoring device also employs light pipes to selectively and controllably route light, it may be advantageous to shape the end of the light pipe with a degree of cylindricity (for example, rather than radially symmetric). Such a configuration may improve the SNR by increasing the efficiency of light transferred from the emitter onto or into the skin of the user while decreasing "stray" light from being detected or collected by the photodetector. In this way, the signal sampled, measured and/or detected by the photodetector consists less of stray light and more of the user's response to such emitted light (signal or data that is representative of the response to the emitted light).

In one embodiment, the components of the optical sensor are positioned on the skin side of the device and arranged or positioned to reduce or minimize the distance between (i) the light source(s) and/or associated detector(s) and (ii) the skin of the user. (See, for example, FIG. 5). Such a configuration may improve the efficiency of light flux coupling between the components of the optical sensor and the user's body. For example, in one embodiment, the light source(s) and/or associated detector(s) are disposed on a flexible or pliable substrate which facilitates the skin side of the device to conform (for example, without additional processing) or be capable of being shaped (or compliant) to conform to the shape of the user's body part (for example, wrist, arm ankle and/or leg) to which the biometric monitoring device is coupled to attached during normal operation so that the light source(s) and/or associated detector(s) are/is close to the skin of the user (i.e., with little to no gap between the skin side of the device and the juxtaposed surface of the skin of the user. (See, FIG. 11). In one embodiment, the light source(s) and/or associated detector(s) are disposed on a Flat Flex Cable or "FFC" or flexible PCB. In this embodiment, the flexible or pliable substrate (for example, FFC or flexible PCB) could connect to a second substrate (for example, PCB) within the device having other components disposed thereon (for example, the data processing circuitry). Optical components of differing heights may be mounted to different "fingers" of flexible substrate and pressed or secured to the housing surface such that the optical components are flush to the housing surface. In one embodiment, the second substrate may be a relative inflexible or non-pliable substrate, fixed within the device, having other circuitry and components (passive and/or active) disposed thereon.

The biometric monitoring device is adapted to be worn or carried on the body of a user. In preferred embodiments including the optical heart rate monitor, the device may be a wrist-worn or arm-mounted accessory such as a watch or bracelet. (See, for example, FIGS. 2-13). In one embodiment, optical elements of the optical heart rate monitor are located on the interior or skin side of the biometric monitoring device, for example, facing the top of the wrist (i.e., the optical heart rate monitor is juxtaposed the wrist) when the device is wrist mounted. (See, for example, FIGS. 2-7).

In another embodiment, the optical heart rate monitor is located on one or more external or environmental side surfaces of the biometric monitoring device. (See, for example, FIGS. 12 and 13). In this embodiment, the user may touch an optical window (behind which optical elements of the optical heart rate monitor are located) with a finger on the opposing hand to initiate a heart rate measurement (and/or other metrics related to heart rate such as heart rate variability) and/or collect data which may be used to determine the user's heart rate (and/or other metrics related to heart rate). (See, for example, FIG. 12). In one embodiment, the biometric monitoring device may trigger or initiate the measurement(s) by detecting a (sudden) drop in incident light on the photodiode—for example, when the user's finger is placed over the optical window. In addition thereto, or in lieu thereof, a heart rate measurement (or other such metric) may be trigged by an IR-based proximity detector and/or capacitive touch/proximity detector (which may be separate from other detectors). Such IR-based proximity detector and/or capacitive touch/proximity detector may be disposed in or on and/or functionally, electrically and/or physically coupled to the optical window to detect or determine the presence of, for example, the user's finger.

In yet another embodiment, the biometric monitoring device may include a button which, when depressed, triggers or initiates heart rate measurement (and/or other metrics related to heart rate). The button may be disposed in close proximity of the optical window to facilitate the user pressing the button while the finger is disposed on the optical window. (See, for example, FIG. 13). In one embodiment, the optical window may be embedded in a push button. Thus, when the user presses the button, it could trigger a measurement via the user's finger which depresses the button. Indeed, the button may be given a shape and/or resistance to pressing that enhances or optimizes a pressure profile against the finger to provide high SNR during measurement or data acquisition. In other embodiments (not illustrated), the biometric monitoring device may take the form of a clip, smooth object, pendant, anklet, belt, etc. that is adapted to be worn on the body, clipped or mounted to an article of clothing, deposited in clothing (e.g., pocket), or deposited in an accessory (e.g., handbag).

In one specific embodiment, the biometric monitoring device includes a protrusion on the skin or interior side of the device. (See, FIG. 2-11). When coupled to the user, the protrusion engages the skin with more force than the surrounding device body. In this embodiment, an optical window or light transmissive structure (both of which are discussed in detail above) may form or be incorporated in a portion of the protrusion. The light emitter(s) and/or detector(s) of the optical sensor may be disposed or arranged in the protrusion juxtaposed the window or light transmissive structure. (See, for example, FIGS. 3 and 11). As such, when attached to the user's body, the window portion of the protrusion of the biometric monitoring device engages the user's skin with more force than the surrounding device body—thereby providing a more secure physical connection between the user's skin and the optical window. That is, a protrusion improves sustained contact between the biometric monitoring device and the user's skin which may reduce the amount of stray light measured by the photodetector, decrease motion between the biometric monitoring device and the user, and/or provide improved local pressure to the user's skin; all of which may increase the quality of the cardiac signal of interest. Notably, the protrusion may contain other sensors that benefit from close proximity and/or secure contact to the user's skin. These may be included in addition to or in lieu of a heart rate sensor and include sensors such as a skin temperature sensor (e.g., noncontact thermopile that utilizes the optical window or thermistor joined with thermal epoxy to the outer surface of the protrusion), pulse oximeter, blood pressure sensor, EMG, or galvanic skin response sensor.

In addition thereto, or in lieu thereof, a portion of the skin side of the biometric monitoring device may include a friction enhancing mechanism or material. For example, the skin side of the biometric monitoring device may include a plurality of raised or depressed regions portions (for example, small bumps, ridges, grooves, and/or divots). Moreover, a friction enhancing material (for example, a gel-like material such as silicone) may be disposed on the skin side. Indeed, a device back made out of gel may also provide friction while also improving user comfort and preventing stray light from entering. As noted above, a friction enhancing mechanism or material may be used alone or in conjunction with the biometric monitoring device having a protrusion as described herein. In this regard, the biometric monitoring device may include a plurality of raised or depressed regions portions (for example, small bumps, ridges, grooves, and/or divots) in or on the protrusion portion of the device. Indeed, such raised or depressed regions portions may be incorporated/embedded in or on a window portion of the protrusion. In addition thereto, or in lieu thereof, the protrusion portion may consist of or be coated with a friction enhancing material (for example, a gel-like material such as silicone). Notably, the use of a protrusion and/or friction may improve measurement accuracy of data acquisition corresponding to certain parameters (e.g., heart rate, heart rate variability, galvanic skin response, skin temperature, skin coloration, heat flux, blood pressure, blood glucose, etc.) by reducing motions of the sensor relative to the user's skin during operation, especially whilst the user is in motion.

Some or all of the interior or skin side housing of the biometric monitoring device may also consist of a metal material (for example, steel, stainless steel, aluminum, magnesium, or titanium). Such a configuration may provide a structural rigidity. (See, for example, FIG. 3.) In this embodiment, the device body may be designed to be hypoallergenic through the use of a hypoallergenic "Nickel-Free" stainless steel. Notably, it may be advantageous to employ (at least in certain locations) a type of metal that is ferrous in properties (for example, a grade of stainless steel that is ferrous). Under this circumstance, the biometric monitoring device (where it includes a rechargeable energy source (for example, rechargeable battery) may interconnect with a charger using magnetic properties to secure thereto. In addition, biometric monitoring device may also engage a dock or dock station using such magnetic properties to facilitate data transfer.

Moreover, such a housing may provide enhanced electromagnetic shielding which would enhance the integrity and reliability of the optical heart rate sensor and data acquisition process/operation. Furthermore, a skin temperature sensor may be physically and thermally coupled, for example with thermal epoxy, to the metal body to sense the temperature of the user. In embodiments including a protrusion, the sensor may be positioned near or in the protrusion to provide secure contact and localized thermal coupling to the user's skin.

In a preferred embodiment, one or more components of the optical sensor (which may, in one embodiment, located in a protrusion, and/or in another embodiment, may be disposed or placed flush to the surface of the device) are attached, fixed, included and/or secured to the biometric monitoring device via a liquid-tight seal (i.e., a method/mechanism that prevents liquid ingress into the body of the biometric monitoring device). For example, in one embodiment, a device back made out of a metal including but not limited to stainless steel, aluminum, magnesium, or titanium or a rigid plastic could provide a structure which is stiff enough to maintain the structural integrity of the device while accommodating a watertight seal for the sensor package. (See, FIGS. 3-7).

In a preferred embodiment, a package or module of the optical sensor would be connected to the device with a pressure sensitive adhesive and a liquid gasket. (See, FIG. 7). Screws, rivets or the like may also be used, for example, if a stronger or more durable connection is required between the optical sensor package/module and the device body. Notably, the present inventions may also use watertight glues, hydrophobic membranes such as Gore-Tex, o-rings, sealant, grease, or epoxy to secure or attach the optical sensor package/module and the device body.

As intimated above, the biometric monitoring device may include a material disposed on the skin or interior side which includes high reflectivity characteristic—for example, to polished stainless steel, reflective paint, and polished plastic. In this way, light scattered off the skin side of the device may be reflected back into the skin in order to, for example, improve the SNR. Indeed, this effectively increases the input light signal as compared with a device body back that is non-reflective. Notably, in one embodiment, the color of the skin or interior side of the biometric monitoring device is selected to provide certain optical characteristics (for example, reflect certain or predetermined wavelengths of light), in order to improve the signal of certain physiological data types. For example, where the skin or interior side of the biometric monitoring is green, the measurements of the heart rate may be enhanced due to the preferential emission of a wavelength of the light corresponding to the green spectrum. Where the skin or interior side of the biometric monitoring is red, the measurements of the SpO2 may be enhanced due to the emission preferential of a wavelength of the light corresponding to the red spectrum. In one embodiment, the color of the skin or interior side of the biometric monitoring may be modified, adjusted and/or controlled in accordance with a predetermined type of physiological data being acquired.

Figure 17:
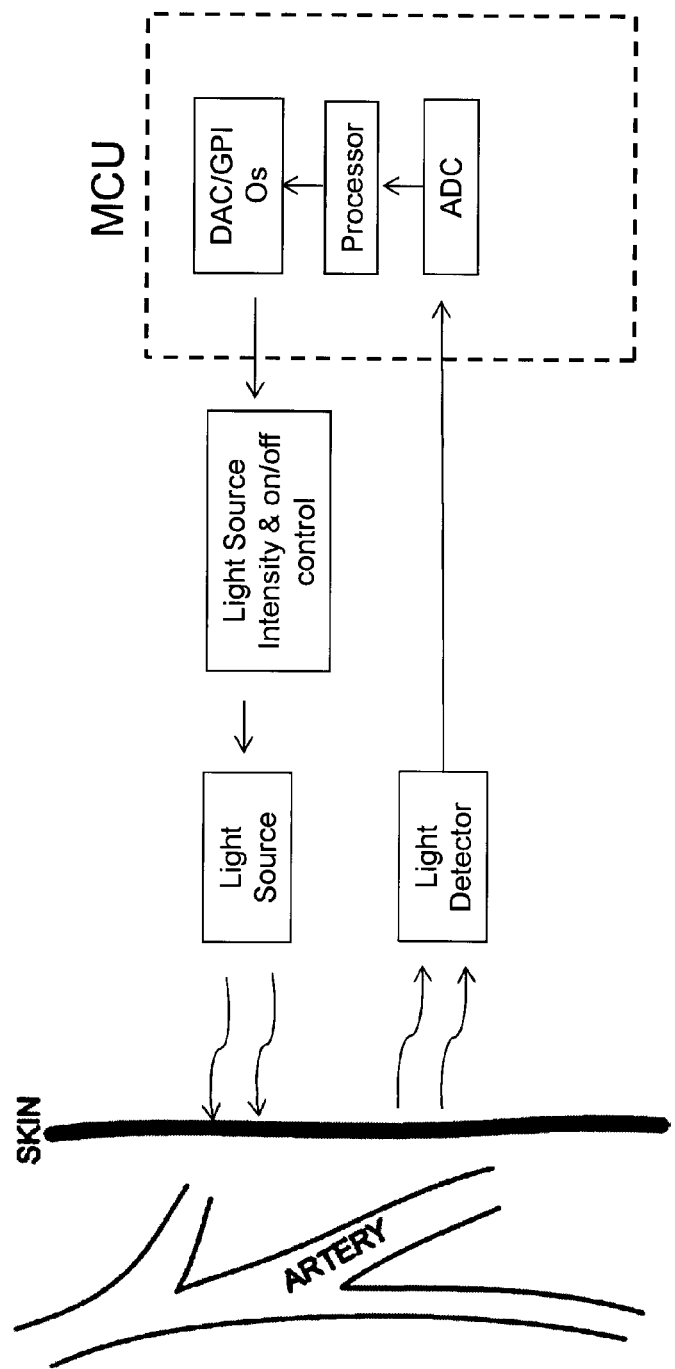
FIG. 17 illustrates an exemplary PPG sensor having a light source, light detector, ADC, processor, DAC/GPIOs, and light source intensity and on/off control.
Figure 18:
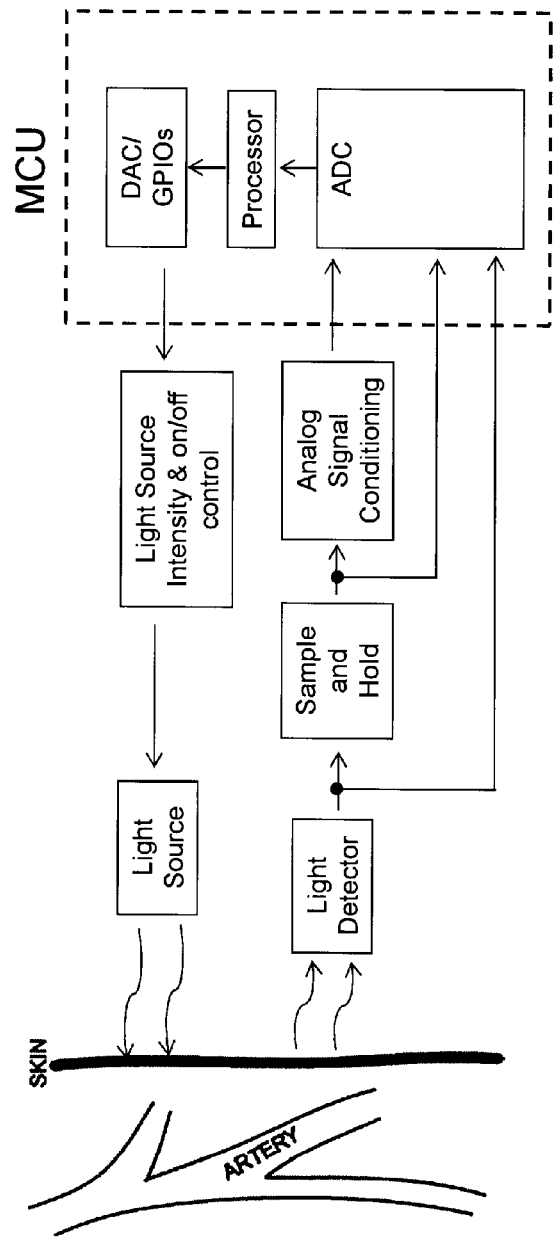
FIG. 18 illustrates an exemplary PPG sensor which is similar to the embodiment illustrated in FIG. 17; in this embodiment, however, the sensor employs a sample and hold circuit as well as analog signal conditioning.
Figure 19:
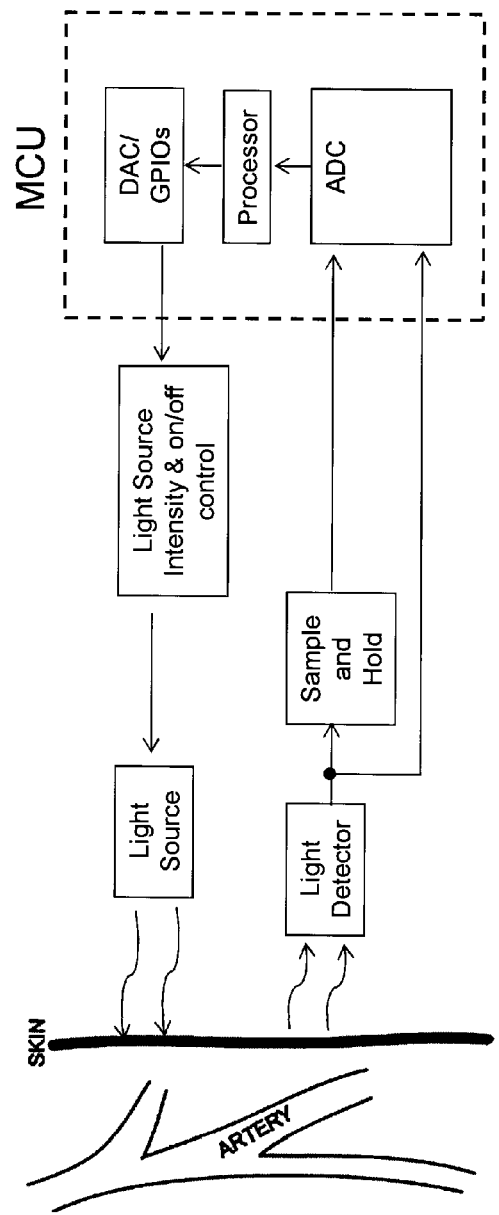
FIG. 19 illustrates an exemplary PPG sensor which is similar to the embodiment illustrated in FIG. 17; in this embodiment, however, the sensor employs a sample and hold circuit (and, in one embodiment, oversamples the signals)
Figure 20:
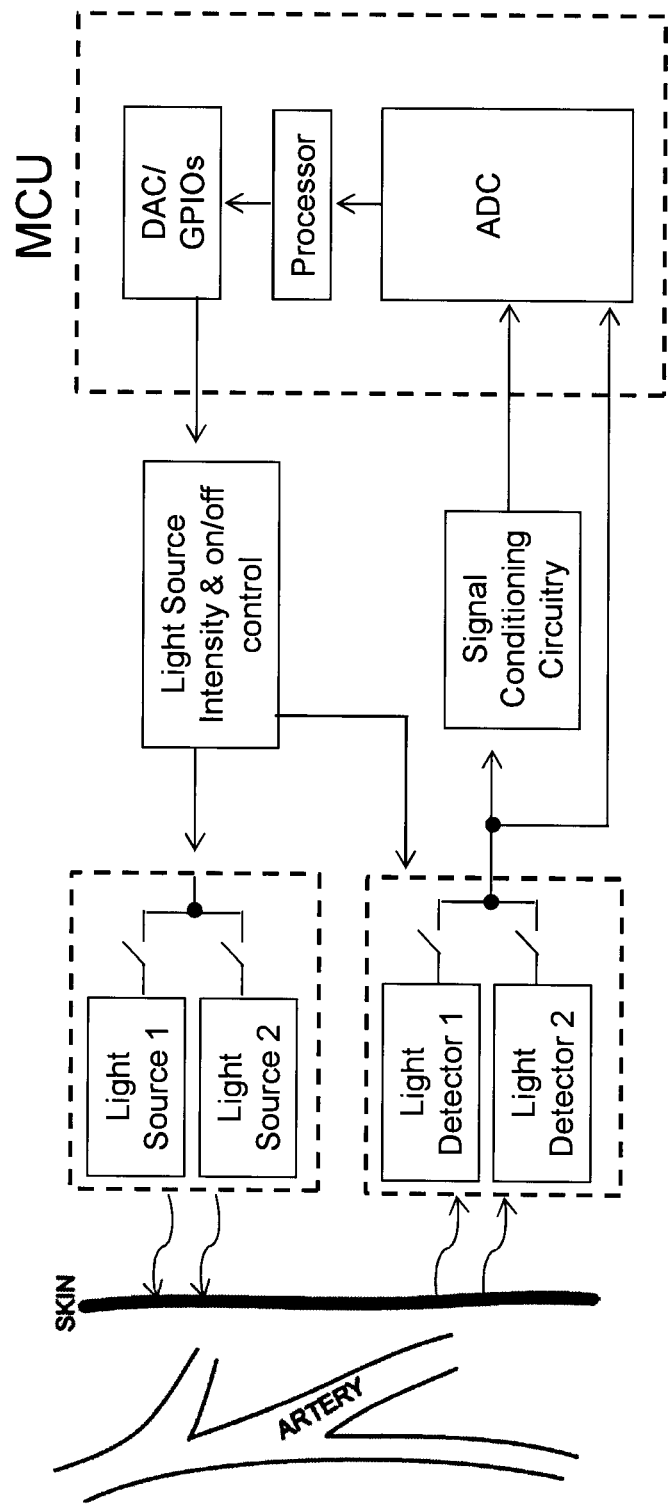
FIG. 20 illustrates an exemplary PPG sensor having multiple switchable light sources and detectors, light source intensity and on/off control, and signal conditioning circuitry
Figure 21:
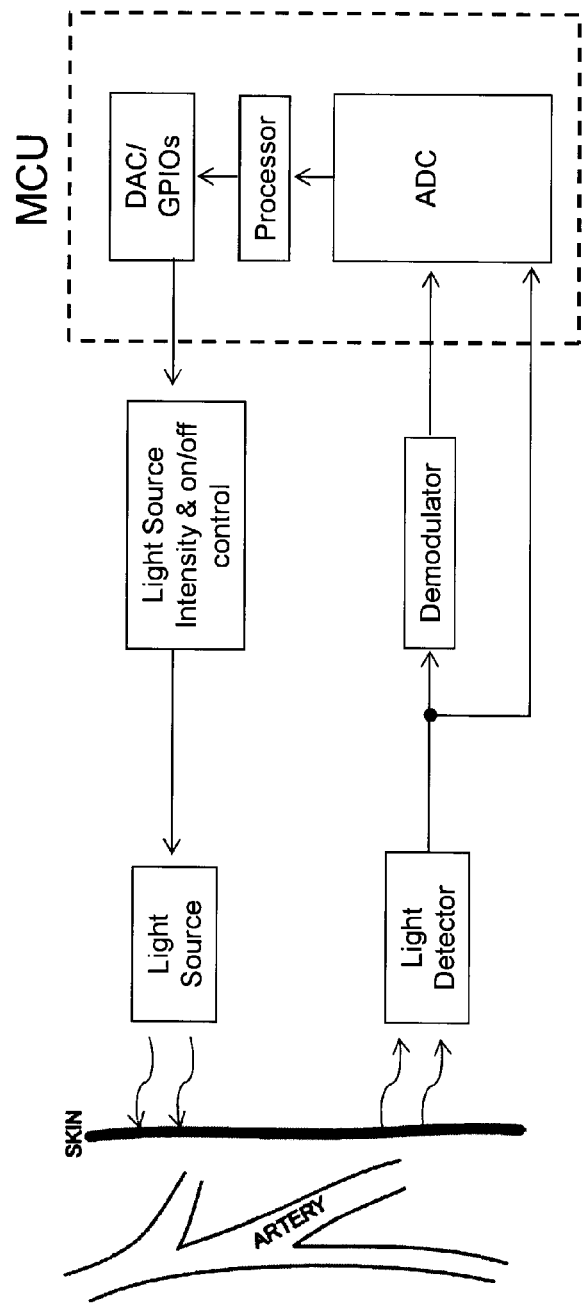
FIG. 21 illustrates an exemplary PPG sensor which uses synchronous detection; notably, in this embodiment, a demodulator is employed to detect/recover the signal.
Figure 22:
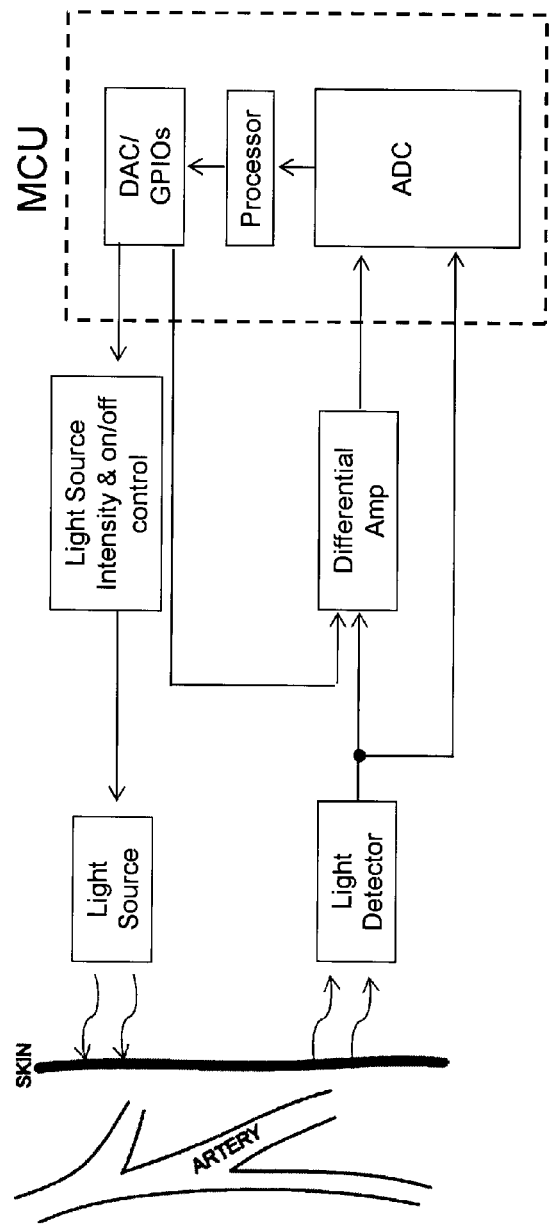
FIG. 22 illustrates an exemplary PPG sensor which is similar to the embodiment illustrated in FIG. 17; in this embodiment, however, the sensor employs a differential amplifier in the signal detection path.
Figure 23:
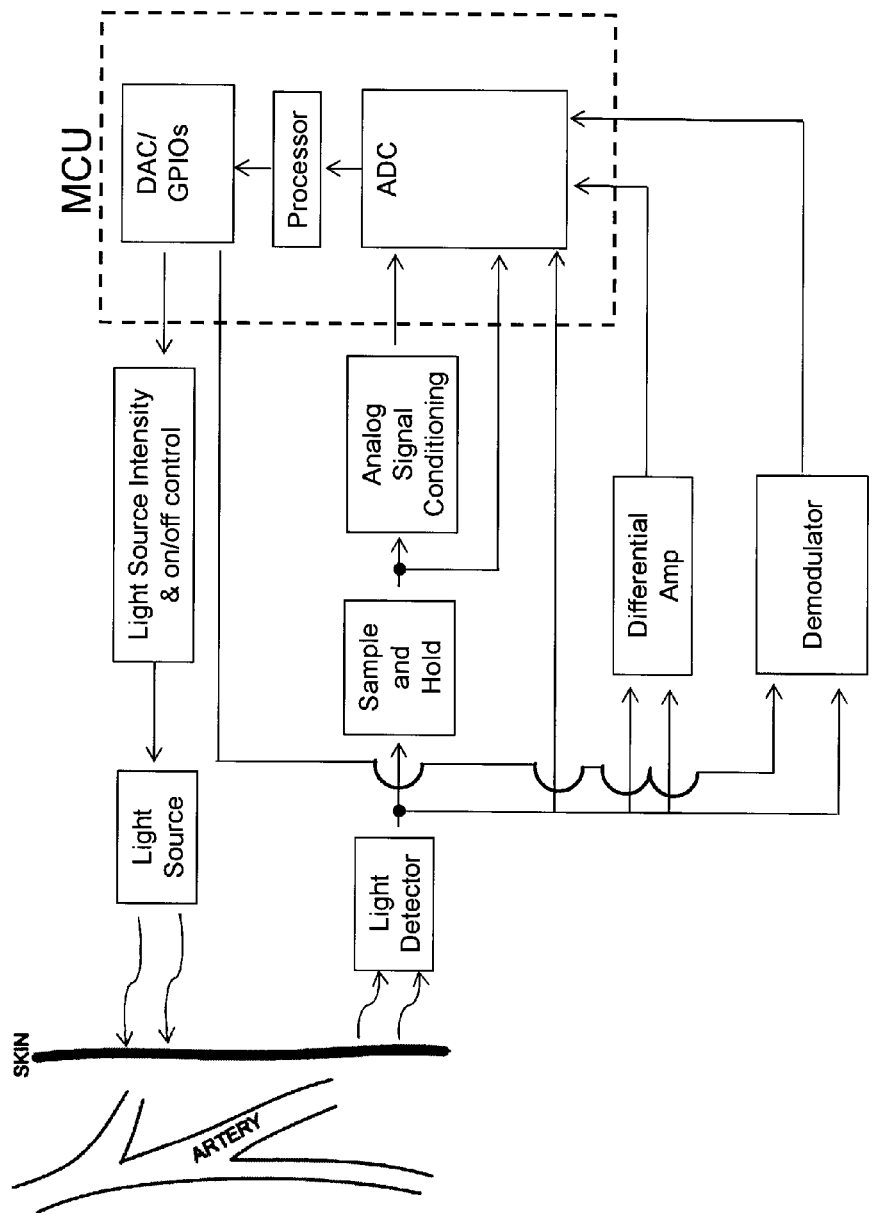
FIG. 23 illustrates an exemplary PPG sensor having many of the features/circuitry illustrated in FIG. 17-22.

FIG. 17 depicts an exemplary schematic block diagram of an optical sensor where light is emitted from a light source toward the user's skin and the reflection is sensed by a light detector, which is subsequently digitized by an analog to digital converter (ADC). The intensity of the light source may be modified (e.g., through a light source intensity control module) to maintain a desirable reflected intensity signal. For example, the light source intensity may be reduced to avoid saturation of the output signal from the light detector. As another example, the light source intensity may be increased to maintain the output signal from the light detector within a desired range of output values. Notably, the active control of the system may be achieved through linear or nonlinear control methods such as proportional-integral-derivative (PID) control, fixed step control, predictive control, neural networks, hysteresis, and the like, and may also employ information derived from other sensors in the device such as motion, galvanic skin response, etc. FIG. 17 is provided for illustration and does not limit the implementation of such a system to, for instance, an ADC integrated within a MCU, or the use of a MCU for that matter. Other possible implementations include the use of one or more internal or external ADCs, FPGAs, ASICs, etc.

In another embodiment, the system may incorporate the use of a sample and hold circuit (or equivalent) to maintain the output of the light detector while the light source is turned off or attenuated to save power. In embodiments of the present inventions where relative changes in the light detector output are of primary importance (e.g., heart rate measurement), the sample and hold circuit may not have to maintain an accurate copy of the output of the light detector. In such cases, the sample and hold may be reduced to, for example, a diode (e.g., Schottky diode) and capacitor. The output of the sample and hold may be presented to an analog signal conditioning circuit (e.g., a Sallen-Key bandpass filter, level shifter, and/or gain circuit) to condition and amplify the signal within frequency bands of interest (e.g., 0.1 Hz to 10 Hz for cardiac or respiratory function) which is then digitized by the ADC. See, for example, FIG. 18.

In operation, this removes the DC and low frequency components of the signal and help resolve the AC component related to heart rate and/or respiration. The embodiment may also include the analog signal conditioning circuitry (not illustrated) for variable gain settings that can be controlled to provide a suitable signal (e.g., not saturated). The performance characteristics (e.g., slew rate and/or gain bandwidth product) and power consumption of the light source, light detector, and/or sample and hold may be significantly higher than the analog signal conditioning circuit to enable fast duty cycling of the light source. In an embodiment, the power provided to the light source and light detector may be controlled separately from the power provided to the analog signal conditioning circuit to provide additional power savings. In another embodiment, the output of the light detector and/or sample and hold may be sampled by an ADC in addition to or in lieu of the analog signal conditioning circuit to control the light intensity of the light source or to measure the physiologic parameters of interest when, for example, the analog signal conditioning circuit is not yet stable after a change to the light intensity setting. Notably, because the physiologic signal of interest is typically small relative to the inherent resolution of the ADC, in some embodiments, the reference voltages and/or gain of the ADC may be adjusted to enhance signal quality, or the ADC may be oversampled. In yet another embodiment, the device may digitize the output of only the sample and hold circuit by, for example, oversampling, adjusting the reference voltages and/or gain of the ADC, or using a high resolution ADC. See, for example, FIG. 19.

In another embodiment, the system may incorporate a differential amplifier to amplify the relative changes in the output of the light detector output. See, for example, FIG. 22. In an embodiment, a digital average or digital lowpass filtered signal is subtracted from the output of the light detector output and amplified before it is digitized by the ADC. In another embodiment, an analog average or analog lowpass filtered signal is subtracted from the output of the light detector through, for example, the use of a sample and hold circuit and analog signal conditioning circuitry. The power provided to the light source, light detector, and differential amplifier may be controlled separately from the power provided to the analog signal conditioning circuit to improve power savings.

In an embodiment, the light detector module may incorporate a transimpedance amplifier stage with variable gain. Such a configuration may avoid or minimize saturation from bright ambient light and/or bright emitted light from the light source. For example, the gain of the transimpedance amplifier may be automatically reduced with a variable resistor and/or multiplexed set of resistors in the negative feedback path of the transimpedance amplifier. In embodiments of the present inventions, the device may incorporate little to no optical shielding from ambient light by amplitude modulating the intensity of the light source and demodulating the output of the light detector (e.g., synchronous detection). See, for instance, FIG. 21. In other aspects, if the ambient light is of sufficient brightness to obtain a heart rate signal, the light source may be reduced in brightness and/or turned off completely.

In yet another embodiment, the aforementioned processing techniques may be used in combination to optically measure physiological parameters of the user. See, for example, FIG. 23. This topology may allow the system to operate in a low power measurement state and circuit topology when applicable and adapt to a higher power measurement state and circuit topology as necessary. For instance, the system may measure the physiologic parameter (e.g., heart rate) of interest using analog signal conditioning circuitry whilst the user is immobile or sedentary to reduce power consumption, but switch to oversampled sampling of the light detector output directly whilst the user is active. There are many inventions described and illustrated herein. While certain embodiments, features, attributes and advantages of the inventions have been described and illustrated, it should be understood that many others, as well as different and/or similar embodiments, features, attributes and advantages of the present inventions, are apparent from the description and illustrations. As such, the above embodiments of the inventions are merely exemplary. They are not intended to be exhaustive or to limit the inventions to the precise forms, techniques, materials and/or configurations disclosed. Many modifications and variations are possible in light of this disclosure.

In embodiments where the device includes a heart rate monitor, processing of the signal to obtain heart rate measurements may comprise filtering and/or signal conditioning such as bandpass filtering (e.g., Butterworth filter). To counteract the large transients that may occur in the signal and/or to improve convergence of said filtering, nonlinear approaches may be employed such as neural networks or slew rate limiting. Data from the sensors on the device such as motion, galvanic skin response, skin temperature, etc., may be used to adjust the signal conditioning methods employed. Under certain operating conditions, the heart rate of the user may be measured by counting the number of signal peaks within a time window or utilizing the fundamental frequency or second harmonic of the signal (e.g., though a fast Fourier transform (FFT)). In other cases, such as motion, FFTs may be performed on the signal and spectral peaks extracted, which are subsequently processed by a multiple target tracker which starts, continues, merges, and deletes tracks of the spectra. In one embodiment, a similar set of operations are performed on the motion signal and the output is used to do activity discrimination (e.g., sedentary, walking, running, sleeping, lying down, sitting, biking, typing, elliptical, weight training) which is used to assist the multiple target tracker. For instance, it may be determined that the user was stationary and has begun to move and this information can be used to preferentially bias the track continuation toward increasing frequencies. Similarly, the activity discriminator may determine that the user has stopped running or is running slower and this information may be used to preferentially bias the track continuation toward decreasing frequencies. Tracking may be achieved with single-scan or multi-scan multi-target tracker topologies such as joint probabilistic data association trackers, multiple hypothesis tracking, nearest neighbor, etc. Estimation and prediction in the tracker may be done through Kalman filters, spline regression, particle filters, interacting multiple model filters, etc. A track selector module uses the output tracks from the multiple spectra tracker and estimates the user's heart rate. The estimate may be taken as the maximum likelihood track, a weight sum of the tracks against their probabilities of being the heart rate, etc. The activity discriminator may furthermore influence the selection and/or fusion to get the heart rate estimate. For instance, if the user is sleeping, sitting, lying down, or sedentary, a prior probability may be skewed toward heart rates in the 40-80 bpm range; whereas if the user is running, jogging, or doing other vigorous exercise, a prior probability may be skewed toward elevated heart rates in the 90-180 bpm range. The influence of the activity discriminator may be based on the speed of the user. The estimate may be shifted toward (or wholly obtained by) the fundamental frequency of the signal when the user is not moving. The track that corresponds to the user's heart rate may be selected based on criteria that is indicative of changes in activity; for instance, if the user begins to walk from being stationary, the track that illustrates a shift toward higher frequency may be preferentially chosen.

The acquisition of a good heart rate signal may be indicated to the user through a display on the biometric monitoring device or another device in wired or wireless communication with the biometric monitoring device (e.g., a Bluetooth Low Energy equipped mobile phone). In a preferred embodiment, the biometric monitoring device includes a signal strength indicator which is represented by the pulsing of a LED that is viewable by the user. The pulsing may be timed or correlated to be coincident with the user's heart beat. The intensity, pulsing rate and/or color of the LED may be modified or adjusted to suggest signal strength. For example, a brighter LED intensity may represent a stronger signal or in a RGB LED configuration, a green colored LED may represent a stronger signal.

In a preferred embodiment, the strength of the heart rate signal may be determined by the energy (e.g., squared cumulative sum) of the signal in a frequency band of, for instance, 0.5 Hz to 4 Hz. In another embodiment, the biometric monitoring device of the present invention may have a strain gauge, pressure sensor, and/or force sensor which may be incorporated or constructed into the housing and/or in the band (in those embodiments where the biometric monitoring device is attached to or mounted with a band like a watch, bracelet, and/or armband—which may then be secured to the user). A signal quality metric may be calculated with these contact sensors either alone or in combination with data from the heart rate signal.

In another embodiment, the biometric monitoring device may monitor heart rate optically through an array of photodetectors such as a grid of photodiodes or a CCD camera. Motion of the optical device with respect to the skin may be tracked through feature tracking of the skin and/or adaptive motion correction using an accelerometer and gyroscope. The detector array may be in contact with the skin or offset at a small distance away from the skin. The detector array and its associated optics may be actively controlled (e.g., with a motor) to maintain a stabilized image of the target and acquire a heart rate signal. This optomechanical stabilization may be achieved using information from motion sensors (e.g., gyroscope) or image features. In one embodiment, the biometric monitoring device may implement relative motion cancellation using a coherent or incoherent light source to illuminate the skin and a photodetector array with each photodetector associated with comparators for comparing the intensity between neighboring detectors—obtaining a so-called speckle pattern which may be tracked using a variety of image tracking techniques such as optical flow, template matching, edge tracking, etc. In this embodiment, the light source used for motion tracking may be different than the light source used in the optical heart rate monitor.

In another embodiment, the biometric monitoring device may consist of a plurality of photodetectors and photoemitters distributed along the surface of the device that touches the user's skin (i.e., the skin side of the biometric monitoring device). (See, for example, FIGS. 2-11). In the example of a bracelet, for instance, there may be a plurality of photodetectors and photoemitters placed along the circumference of the interior of the band. (See, for example, FIG. 11). A heart rate signal quality metric at each site may be calculated to determine the best or set of best sites for estimating the user's heart rate. Subsequently, some of the sites may be disabled or turned off to, for example, reduce power consumption. The device may periodically check the heart rate signal quality at some or all of the sites to enhance, monitor and/or optimize signal and/or power efficiency.

In another embodiment, biometric monitoring device of the present invention may include a heart rate monitoring system including a plurality of sensors such as optical, acoustic, pressure, electrical (e.g., EKG), and motion and fuse the information from two or more of these sensors to provide an estimate of heart rate and/or mitigate noise induced from motion.

In addition to heart rate monitoring (or other biometric monitoring), or in lieu thereof, the biometric monitoring device, in one embodiment, includes optical sensors to track or detect time and duration of ultraviolet light exposure, total outdoor light exposure, the type of light source and duration and intensity of that light source (fluorescent light exposure, incandescent bulb light exposure, halogen, etc), exposure to television (based on light type and flicker rate), whether the user is indoors or outdoors, time of day and location based on light conditions. In one embodiment, the ultraviolet detection sensor may consist of a reverse biased LED emitter driven as a light detector. The photocurrent produced by this detector may be characterized by, for instance, measuring the time it takes for the LED's capacitance (or alternately a parallel capacitor) to discharge.

All of the optical sensors could be used in conjunction with other sensors to improve detection of the data described above or be used to augment detection of other types of physiological or environmental data.

Where the biometric monitoring device includes an audio or passive acoustic sensor, the device may contain one or more passive acoustic sensors that detect sound and pressure and which can include but not be limited to microphones, piezo film, etc. The acoustic sensors may be disposed on one or more sides of the device, including the side that touches or faces the skin (skin side) and the sides that face the environment (environmental sides).

The biometric monitoring device of the present invention may also include galvanic skin response (GSR) circuitry to measure the response of the user's skin to emotional and physical stimuli or physiological changes (e.g., the transition of sleep stage). In one embodiment, the invention is a wrist or arm-mounted device incorporating a band comprised of conductive rubber or fabric so that the galvanic skin response electrodes may be hidden in the band. Because the galvanic skin response circuitry may be subjected to changing temperatures and environmental conditions, it may also include circuitry to enable automatic calibration, such as two or more switchable reference resistors in parallel or series with the human skin/electrode path that allows real-time measurement of known resistors to characterize the response of the galvanic skin response circuit. The reference resistors may be switched into and out of the measurement path such that they are measured independently and/or simultaneously with the human skin.

The skin side sensors would detect any type of sound transmitted through the body and the sensors could be arranged in an array or pattern that optimizes both the SNR and power consumption. These sensors could detect respiration (by listening to the lung), respiratory sounds (breathing, snoring) and problems, heart rate (listening to the heart beat), user's voice (via sound transmitted from the vocal cords throughout the body)

Environmental Sensors

The biometric monitoring device of the present inventions may use one, some or all of the following environmental sensors to, for example, acquire the environmental data, including environmental data outlined in the table below. The biometric monitoring device is not limited to the number or types of sensors specified below but may employ other sensors that acquire environmental data outlined in the table below. All combinations and permutations of environmental sensors and/or environmental data are intended to fall within the scope of the present inventions. Additionally, the device may derive environmental data from the corresponding sensor output data, but is not limited to the types of environmental data that it could derive from said sensor.

Notably, the biometric monitoring device of the present inventions may one or more, or all of the environmental sensors described herein and one or more, or all of the physiological sensors described herein. Indeed, biometric monitoring device of the present inventions may acquire any or all of the environmental data and physiological data described herein using any sensor now known or later developed—all of which are intended to fall within the scope of the present inventions.

TABLE

| Environmental Sensors | Environmental data acquired |
|---|---|
| Motion Detector<br>Potential Embodiments:<br>Inertial, Gyro or Accelerometer<br>GPS | Location |
| Pressure/Altimeter sensor | Elevation |
| Ambient Temp | temperature |
| Light Sensor | Indoor vs outdoor<br>Watching TV (spectrum/<br>flicker rate detection)<br>Optical data transfer-initiation,<br>QR codes, etc.<br>ultraviolet light exposure |
| Audio | Indoor vs Outdoor |
| Compass<br>Potential Embodiments:<br>3 Axis Compass | Location |

In one embodiment, the biometric monitoring device may include an altimeter sensor, for example, disposed or located in the interior of the device housing. (See, for example, FIGS.

25 and 26). In such a case, the device housing may have a vent that allows the interior of the device to measure, detect, sample and/or experience any changes in exterior pressure. In one embodiment, the vent prevents water from entering the device while facilitating measuring, detecting and/or sampling changes in pressure via the altimeter sensor. For example, an exterior surface of the biometric monitoring device may include a vent type configuration or architecture (for example, a Gore™ vent) which allows ambient air to move in and out of the housing of the device (which allows the altimeter sensor to measure, detect and/or sample changes in pressure), but reduces, prevents and/or minimizes water and other liquids flow into the housing of the device.

The altimeter sensor, in one embodiment, may be filled with gel that allows the sensor to experience pressure changes outside of the gel. The use of a gel filled altimeter may give the device a higher level of environmental protection with or without the use of an environmentally sealed vent. The device may have a higher survivability rate with a gel filled altimeter in locations including but not limited to those that have high humidity, a clothes washer, a dish washer, a clothes dryer, a steam room, the shower, a pool, and any location where the device may be exposed to moisture, exposed to liquid or submerged in liquid.

Sensors Integration/Signal Processing

The biometric monitoring device of the present invention may use data from two or more sensors to calculate the corresponding physiological or environmental data as seen in the table below (for example, data from two or more sensors which are used in combination). The device may include but is not limited to the number, types, or combinations of sensors specified below. Additionally, the device may derive the included data from the corresponding sensor combinations, but is not limited to the number or types of data that could be calculated from the corresponding sensor combinations.

TABLE

| Sensor Integrations | Data derived from signal processing of multiple sensors |
| --- | --- |
| Skin Temp and Ambient Temp | Heat Flux |
| Heart Rate and Motion | Elevation gain |
| Motion detector and other user's motion detector | Users in the proximity |
| Motion, any heart rate sensor, galvanic skin response | Sit/Standing detection |
| Any heart rate, heart rate variability sensor, respiration, motion | Sleep Phase detection<br>Sleep Apnea detection |
| Any heart rate sensor and/or wetness sensor, and/or motion detector | Resting Heart rate<br>Active Heart Rate<br>Heart rate while asleep<br>Heart rate while sedentary |
| Any heart rate detector | Early detection of heart problems:<br>cardiac Arrhythmia<br>Cardiac arrest |
| Multiple heart rate detectors | Pulse transit time |
| Audio and/or strain gauge | Typing detection |
| GPS and photoplethysmography (PPG) | location-stress correlation:<br>determination of stressful regions<br>determination of low stress regions<br>Activity specific heart rate<br>resting heart rate<br>active heart rate<br>Automatic activity classification and activity heart rate determination |
| Heart rate, galvanic skin response, accelerometer and respiration | User fatigue, for example while exercising |

Figure 16:
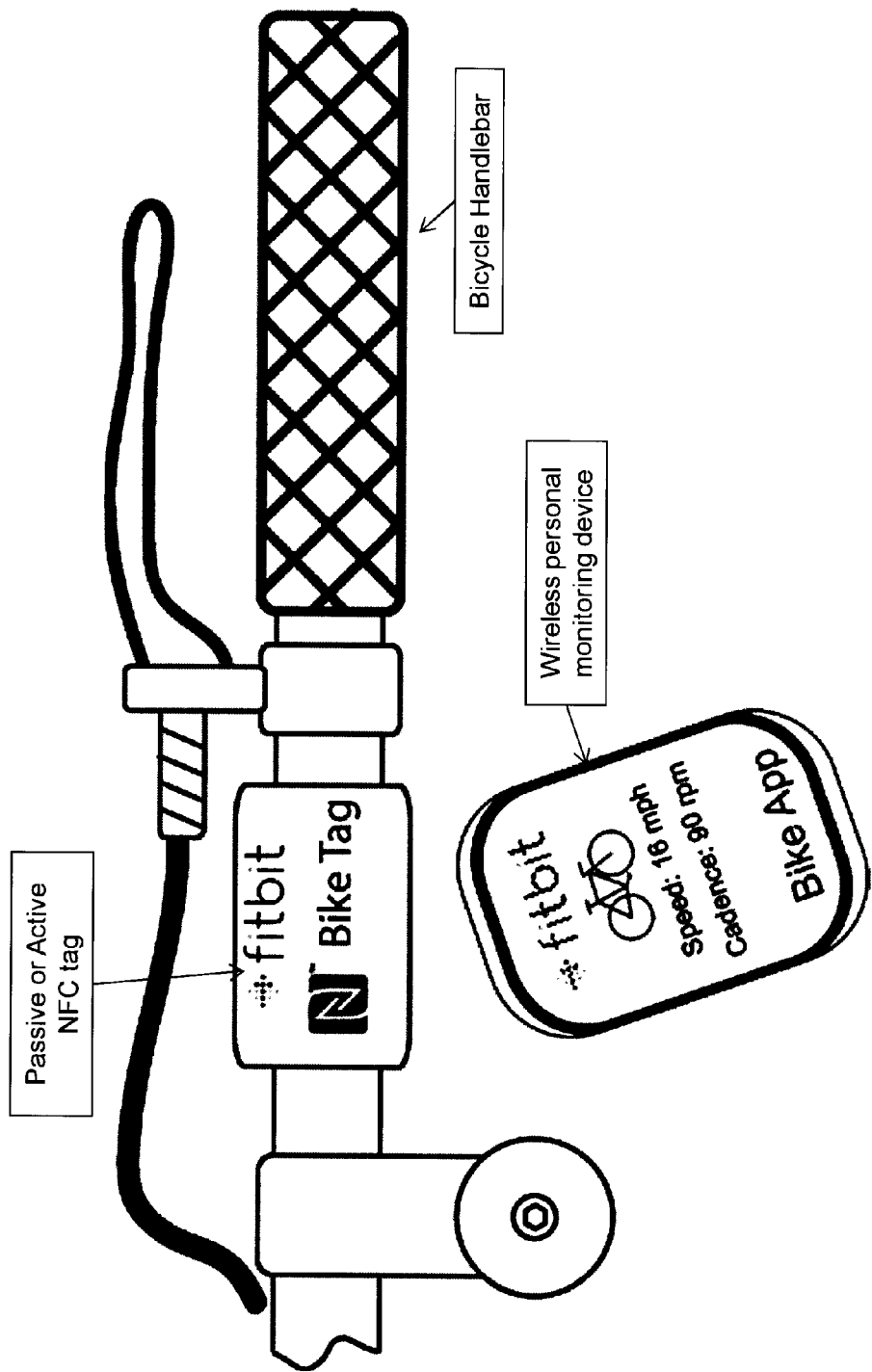
FIG. 16 illustrates an exemplary portable monitoring device which has a bicycle application (resident thereon) which may display speed and/or cadence among other metrics; the application may be activated whenever the monitoring device comes into proximity of a passive or active NFC tag, which may be attached to or disposed on the bicycle, for example, the bicycle handlebar(s), frame and/or pedal(s)

In one embodiment, the device may also include a near-field communication (NFC) receiver/transmitter to detect proximity to another device, such as a mobile phone. When the device is brought into close or detectable proximity to the second device, it may trigger the start of new functionality on the second device (e.g., the launching of an "app" on the mobile phone and radio syncing of physiological data from the device to the second device). (See, for example, FIG. 16). Indeed, the biometric monitoring device of the present invention may implement any of the circuitry and techniques described and/or illustrated in U.S. Provisional Patent Application 61/606,559, filed Mar. 5, 2012, "Near Field Communication System, and Method of Operating Same", inventor: James Park (the contents of which are incorporated herein by reference).

Figure 26:
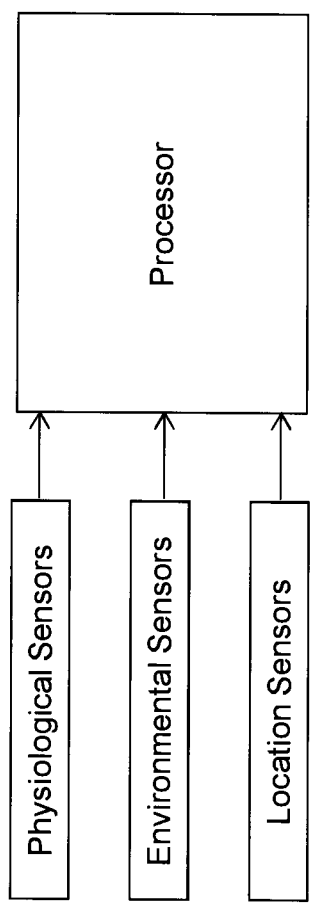
FIG. 26 illustrates certain circuitry/elements of an exemplary portable monitoring device having physiological sensors, environmental sensors, and/or location sensors connected to a processor.
Figure 27:
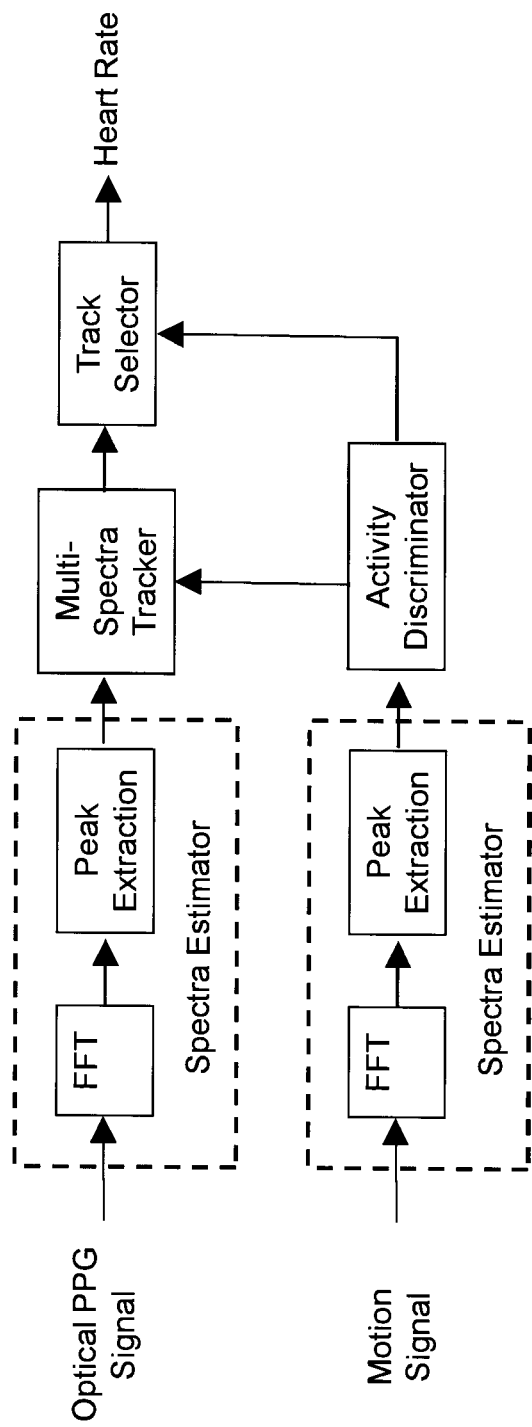
FIG. 27 illustrates, in block diagram form, exemplary signal flow of motion signals and optical PPG signals which are employed to measure a heart rate of the user.
Figure 28:
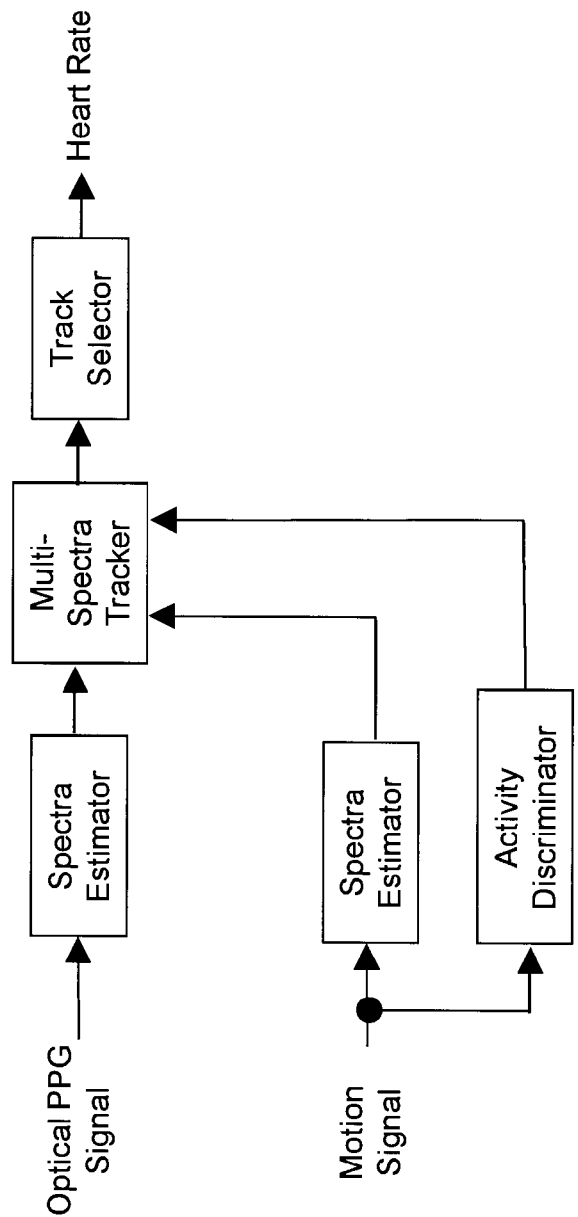
FIG. 28 illustrates, in block diagram form, exemplary signal flow of motion signals and optical PPG signals which are employed to measure a heart rate of the user.
Figure 29:
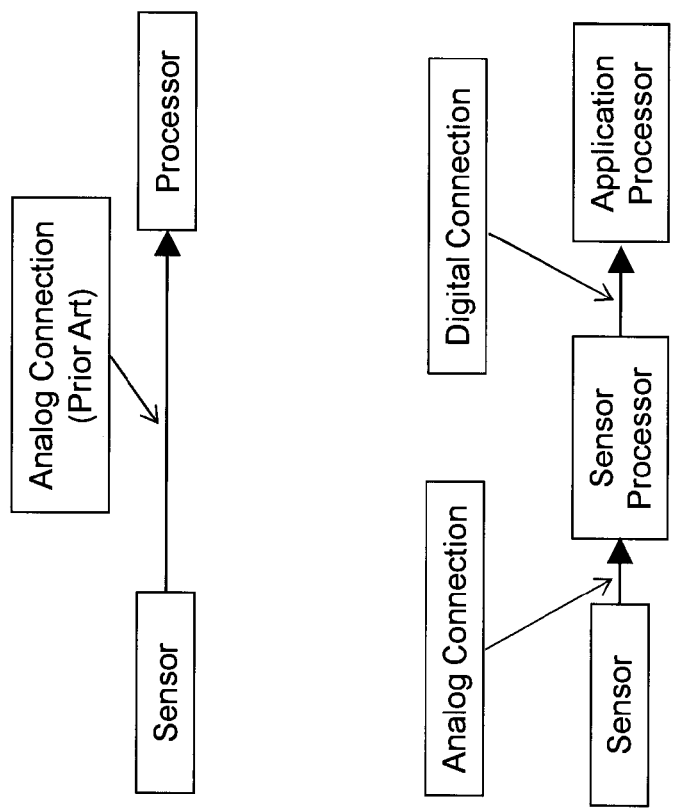
FIG. 29 illustrates a sensor which has an analog connection to a sensor processor which, in turn, has a digital connection to an application processor.
Figure 30:
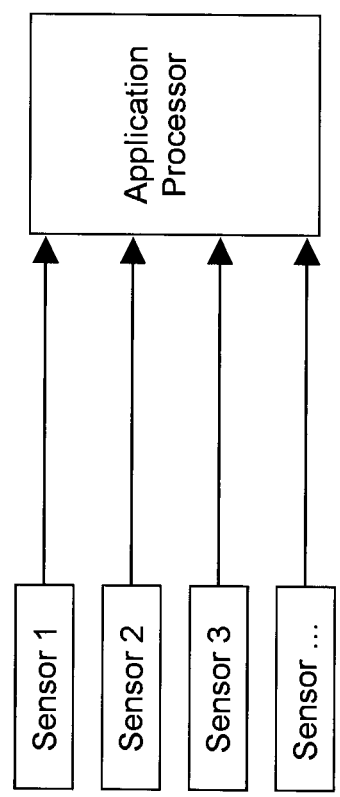
FIG. 30 illustrates a sensor device which has one or multiple sensors connected to an application processor.
Figure 31:
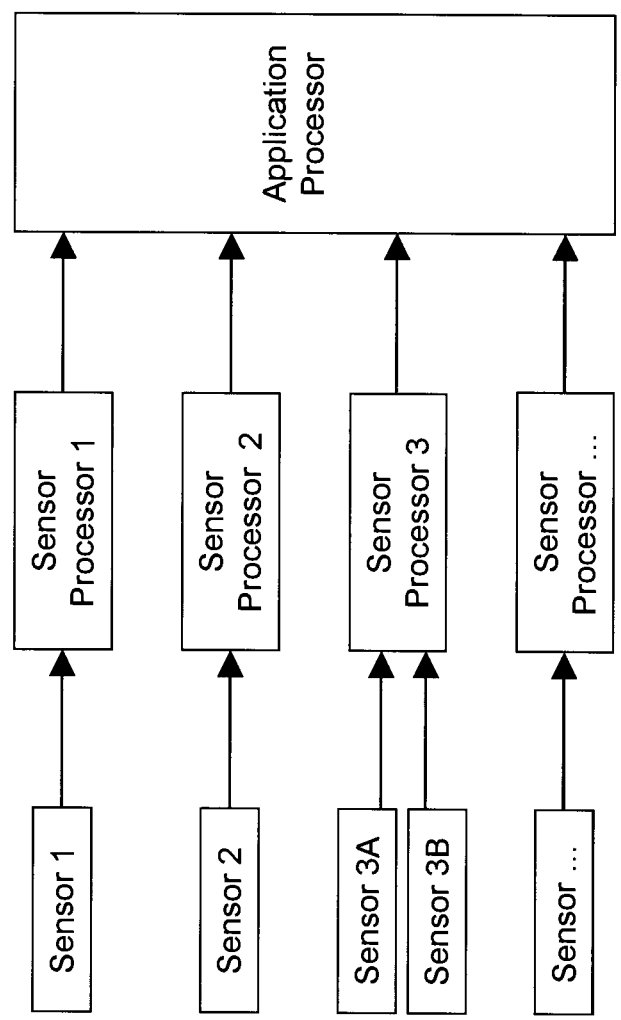
FIG. 31 illustrates a sensor device which has one or multiple sensors connected to sensor processors which, in turn, are connected to an application processor.

In another embodiment, the biometric monitoring device includes a location sensor (for example, GPS circuitry) and heart rate sensor (for example, photoplethysmography circuitry) to generate GPS or location related data and heart rate related data, respectively. (See, for example, FIGS. 25 and 26). The biometric monitoring device may then fuse, process and/or combine data from these two sensors/circuitry to, for example, determine, correlate and/or "map" geographical regions according to physiological data (for example, heart rate, stress, activity level, quantity of sleep and/or caloric intake). In this way, the biometric monitoring device may identify geographical regions that increase or decrease a measurable user metric including but not limited to heart rate, stress, activity, level, quantity of sleep and/or caloric intake.

In addition thereto, or in lieu thereof, the biometric monitoring device may employ the GPS related data and photoplethysmography related data (notably, each of which may be considered data streams), to determine or correlate the user's heart rate according to activity levels—for example, as determined by the user's acceleration, speed, location and/or distance traveled (as measured by the GPS and/or determined from GPS related data). (See, for example, FIGS. 25 and 26). Here, in one embodiment, heart rate as a function of speed may be "plotted" for the user, or the data could be broken down into different levels including but not limited to sleeping, resting, sedentary, moderately active, active, and highly active.

Indeed, the biometric monitoring device may also correlate GPS related data to a database of predetermined geographic locations that have activities associated with them for a set of predetermined conditions. For example, activity determination and corresponding physiological classification (for example, heart rate classification) may include correlating a user's GPS coordinates that correspond to location(s) of exercise equipment, health club and/or gym and physiological data. Under these circumstances, a user's heart rate during, for example a gym workout, may be automatically measured and displayed. Notably, many physiological classifications may be based on GPS related data including location, acceleration, altitude, distance and/or velocity. Such a database including geographic data and physiological data may be compiled, developed and/or stored on the biometric monitoring device and/or external computing device. Indeed, in one embodiment, the user may create their own location database or add to or modify the location database to better classify their activities.

In another embodiment, the user may simultaneously wear multiple biometric monitoring devices (having any of the features described herein). The devices of this embodiment may communicate with each other or a remote device using wired or wireless circuitry to calculate, for example, biometric or physiologic qualities or quantities that, for example, may be difficult or inaccurate to calculate otherwise such as pulse transit time. The use of multiple sensors may also improve the accuracy and/or precision of biometric measurements over the accuracy and/or precision of a single sensor. For example, having a device on the waist, wrist, and ankle could improve the detection of the user taking a step over that of a single device in only one of those locations. Signal processing could be performed on the devices in a distributed or centralized method to provide improved measurements over that of a single device. This signal processing could also be performed remotely and communicated back to the devices after processing.

Processing Task Delegation

The biometric monitoring device may include one or more processors. (See, for example, FIGURES L and M). For example, an independent application processor may be used to store and execute applications that utilize sensor data acquired and processed by one or more sensor processors (processor(s) that process data from physiological, environmental and/or activity sensors). In the case where there are multiple sensors, there may also be multiple sensor processors. An application processor may have sensors directly connected to it as well. Sensor and application processors may exist as separate discrete chips or exist within the same packaged chip (multi-core). A device may have a single application processor, or an application processor and sensor processor, or a plurality of application processors and sensor processors.

In one embodiment, the sensor package could be placed on a daughterboard that consists of all of the analog components. This board may have some of the electronics typically found on the main PCB such as, but not limited to, transimpedance amplifiers, filtering circuits, level shifters, sample and hold circuits, and a microcontroller unit. Such a configuration may allow the daughterboard to be connected to the main PCB through the use of a digital connection rather than analog in addition to any necessary power or ground connections. A digital connection may have a variety of advantages over the analog daughter to main PCB connection including but not limited to a reduction in noise and a reduction in the number of necessary cables. The daughterboard may be connected to the main board through the use of a flex cable or set of wires.

Multiple applications can be stored on an application processor. An application can consist of executable code and data for the application, but not limited to these. Data can consist of graphics or other information required to execute the application or it can be information output generated by the application. The executable code and data for the application can both reside on the application processor or the data for the application can be stored and retrieved from an external memory. External memory may include but is not limited to NAND flash, NOR flash, flash on another processor, other solid-state storage, mechanical or optical disks, RAM.

The executable code for an application can also be stored on an external memory. When an application is requested to be executed, the application processor retrieves the executable code and/or data from the external storage and executes it. The executable code can be temporarily or permanently stored on the memory or storage of the application processor. This allows the application to be executed more quickly on the next execution request, since the step of retrieval is eliminated. When the application is requested to be executed, the application processor can retrieve all of the executable code of the application or portions of the executable code. In the latter case, only the portion of executable code required at that moment is retrieved. This allows applications that are larger than the application processor's memory or storage to be executed.

The application processor can also have memory protection features to prevent applications from overwriting, corrupting, interrupting, blocking, or otherwise interfering with other applications, the sensor system, the application processor, or other components of the system.

Applications can be loaded onto the application processor and any external storage via a variety of wired, wireless, optical, capacitive mechanisms including but not limited to USB, Wi-Fi, Bluetooth, Bluetooth Low Energy, NFC, RFID, Zigbee.

Applications can be cryptographically signed with an electronic signature. The application processor can restrict the execution of applications to those that have the correct signature.

Methods of Wearing the Device

The biometric monitoring device may include a housing having a size and shape that facilitates fixing the device to the user's body during normal operation wherein the device, when coupled to the user, does not measurably or appreciably impact the user's activity. The device may be worn in different ways depending on the specific sensor package integrated into the device and the data that the user would like to acquire.

A user may wear one or more of the biometric monitoring devices of the present invention on their wrist or ankle (or arm or leg) with the use of a band that is flexible and thereby readily fitted to the user. The band may have an adjustable circumference, therefore allowing it to be fitted to the user. The band may be constructed from a material that shrinks when exposed to heat, therefore allowing the user to create a custom fit. The band may be detachable from the "electronics" portion of the biometric monitoring device and, if necessary, replaceable.

In a preferred embodiment, the biometric monitoring device consists of two major components—a body (containing the "electronics") and a band (that facilitates attaching the device to the user). The body may include a housing (made, for example, of a plastic or plastic-like material) and extension tabs projecting from the body (made, for example, from a metal or metal-like material). (See, for example, FIGS. 4-7). The band (made, for example, of a thermoplastic urethane) is attachable to the body mechanically or adhesively. The band may extend out a fraction of the circumference of the user's wrist. The distal ends of the urethane band may be connected with a Velcro, a hook and/or loop elastic fabric band that loops around a D-Ring on one side and then attaches back to itself. In this embodiment, the closure mechanism would allow the user infinite band length adjustment (unlike an indexed hole and mechanical clasp closure). The Velcro or fabric could be attached to the band in a manner that allows it to be replaced (for example, if it is worn or otherwise undesirable to wear before the useful or end of life of the device). In one embodiment, the Velcro or fabric would be attached with screws or rivets and/or glue, adhesive and/or clasp to the band.

The biometric monitoring device of the present invention may also be integrated and worn in a necklace, chest band, bra, patch, glasses, earring, or toe band. The device may be built in such a way that the sensor package/portion of the biometric monitoring device is removable and can be worn in any number of ways including, but not limited to, those listed above.

In another embodiment, the biometric monitoring device of the present invention may be worn clipped to an article of clothing or deposited in clothing (e.g., pocket) or an accessory (e.g., handbag, backpack, wallet). Because the biometric monitoring device may not be near the user's skin, in embodiments that include heart rate measurements, the measurements may be obtained in a discrete, "on demand" context by the user manually placing the device into a specific mode (e.g., depressing a button, covering a capacitive touch sensor, etc., possibly with the heart rate sensor embedded in the button/sensor) or automatically once the user places the device against the skin (e.g., applying the finger to an optical heart rate sensor).

User Interface with the Device

The biometric monitoring device may include one or more methods of interacting with the device either locally or remotely.

In one embodiment, the biometric monitoring device may convey data visually through a digital display. The physical embodiment of this display may use any one or a plurality of display technologies including, but not limited to one or more of LED, LCD, AMOLED, E-Ink, Sharp display technology, graphical display, and other display technologies such as TN, HTN, STN, FSTN, TFT, IPS, and OLET. This display could show data acquired or stored locally on the device or could display data acquired remotely from other devices or Internet services. The device may use a sensor (for example, an Ambient Light Sensor, "ALS") to control or adjust screen backlighting. For example, in dark lighting situations, the display may be dimmed to conserve battery life, whereas in bright lighting situations, the display may increase its brightness so that it is more easily read by the user.

In another embodiment, the device may use single or multicolor LEDs to indicate a state of the device. States that the device indicate may include but are not limited to biometric states such as heart rate or application states such as an incoming message, a goal has been reached. These states may be indicated through the LED's color, being on, off, an intermediate intensity, pulsing (and/or rate thereof), and/or a pattern of light intensities from completely off to highest brightness. In one embodiment, an LED may modulate its intensity and/or color with the phase and frequency of the user's heart rate.

In a preferred embodiment, the use of an E-Ink display would allow the display to remain on without the battery drain of a non-reflective display. This "always-on" functionality may provide a pleasant user experience in the case of, for example, a watch application where the user may simply glance at the device to see the time. The E-Ink display always displays content without comprising the battery life of the device, allowing the user to see the time as they would on a traditional watch.

The device may use a light such as an LED to display the heart rate of the user by modulating the amplitude of the light emitted at the frequency of the user's heart rate. The device may depict heart rate zones (e.g., aerobic, anaerobic) through the color of an LED (e.g., green, red) or a sequence of LEDs that light up in accordance with changes in heart rate (e.g., a progress bar). The device may be integrated or incorporated into another device or structure, for example, glasses or goggles, or communicate with glasses or goggles to display this information to the user.

The biometric monitoring device may also convey information to a user through the physical motion of the device. One such embodiment of a method to physically move the device is the use of a vibration inducing motor. The device may use this method alone, or in combination with a plurality of motion inducing technologies.

The device may convey information to a user through audio. A speaker could convey information through the use of audio tones, voice, songs, or other sounds.

These three information communication methods—visual, motion, and auditory—may be used alone or in any combination with each other or another method of communication to communicate any one or plurality of the following information in the below table:

TABLE

That a user needs to wake up at certain time
That a user should wake up as they are in a certain sleep phase
That a user should go to sleep as it is a certain time
That a user should wake up as they are in a certain sleep phase and in a preselected time window bounded by the earliest and latest time that the user wants to wake up.
An email was received
The user has been inactive for a certain period of time. Notably, this may integrate with other applications like, for instance, a meeting calendar or sleep tracking application to block out, reduce, or adjust the behavior of the inactivity alert.
The user has been active for a certain period of time
The user has an appointment or calendar event
The user has reached a certain activity metric
The user has gone a certain distance
The user has reached a certain mile pace
The user has reached a certain speed
The user has accumulated a certain elevation gain
The user has taken a certain number of steps
The user has had a heart rate measurement recently
The user's heart rate has reached a certain level
The user has a normal, active, or resting heart rate of a specific value or in a specific range
The heart rate has enter or exited a certain goal range or training zone
The user has a new heart rate "zone" goal to reach, as in the case of heart rate zone training for running, bicycling, swimming, etc. activities
The user has swum a lap or completed a certain number of laps in a pool
An external device has information that needs to be communicated to the user such as an incoming phone call or any one of the above alerts
The user has reached a certain fatigue goal or limit. In one embodiment, fatigue may be determined through a combination of heart rate, galvanic skin response, motion sensor, and/or respiration data These examples are provided for illustration and are not intended to limit the scope of information that may be communicated by the device (for example, to the user). Note that the data used to determine whether or not an alert is met may be acquired from a first device and/or one or more secondary devices. The device itself may determine whether the criteria for an alert has been met. Alternatively, a computing device in communication with the device (e.g. a server and/or a mobile phone) may determine when the alert should occur. In view of this disclosure, other information that the device may communicate to the user can be envisioned by one of ordinary skill in the art. For example, the device may communicate with the user when a goal has been met. The criteria for meeting this goal may be based on physiological, contextual, and environmental sensors on a first device, and/or other sensor data from one or more secondary devices. The goal may be set by the user or may be set by the device itself and/or another computing device in communication with the device (e.g. a server). In an exemplary embodiment, the device may vibrate when a biometric goal is met.

The biometric monitoring device of the present invention may be equipped with wireless and/or wired communication circuitry to display data on a secondary device in real time. For example, the invention may be able to communicate with a mobile phone via Bluetooth Low Energy in order to give real-time feedback of heart rate, heart rate variability, and/or stress to the user. The invention may coach or grant "points" for the user to breathe in specific ways that alleviate stress. Stress may be quantified or evaluated through heart rate, heart rate variability, skin temperature, changes in motion-activity data and/or galvanic skin response.

The biometric monitoring device may receive input from the user through one or more local or remote input methods. One such embodiment of local user input could use a sensor or set of sensors to translate a user's movement into a command to the device. Such motions could include but may not be limited to tapping, rolling the wrist, flexing one or more muscles, and swinging. Another user input method may be through the use of a button of type, but not limited to the types, capacitive touch button, capacitive screen, and mechanical button. In one embodiment, the user interface buttons may be made of metal. In the case that the screen uses capacitive touch detection, it may always be sampling and ready to respond to any gesture or input without an intervening event such as pushing a physical button. The device may also take input through the use of audio commands. All of these input methods may be integrated into the device locally or integrated into a remote device that can communicate with the device either through a wired or wireless connection. In addition, the user may also be able to manipulate the device through a remote device. In one embodiment, this remote device could have Internet connectivity.

Figure 14:
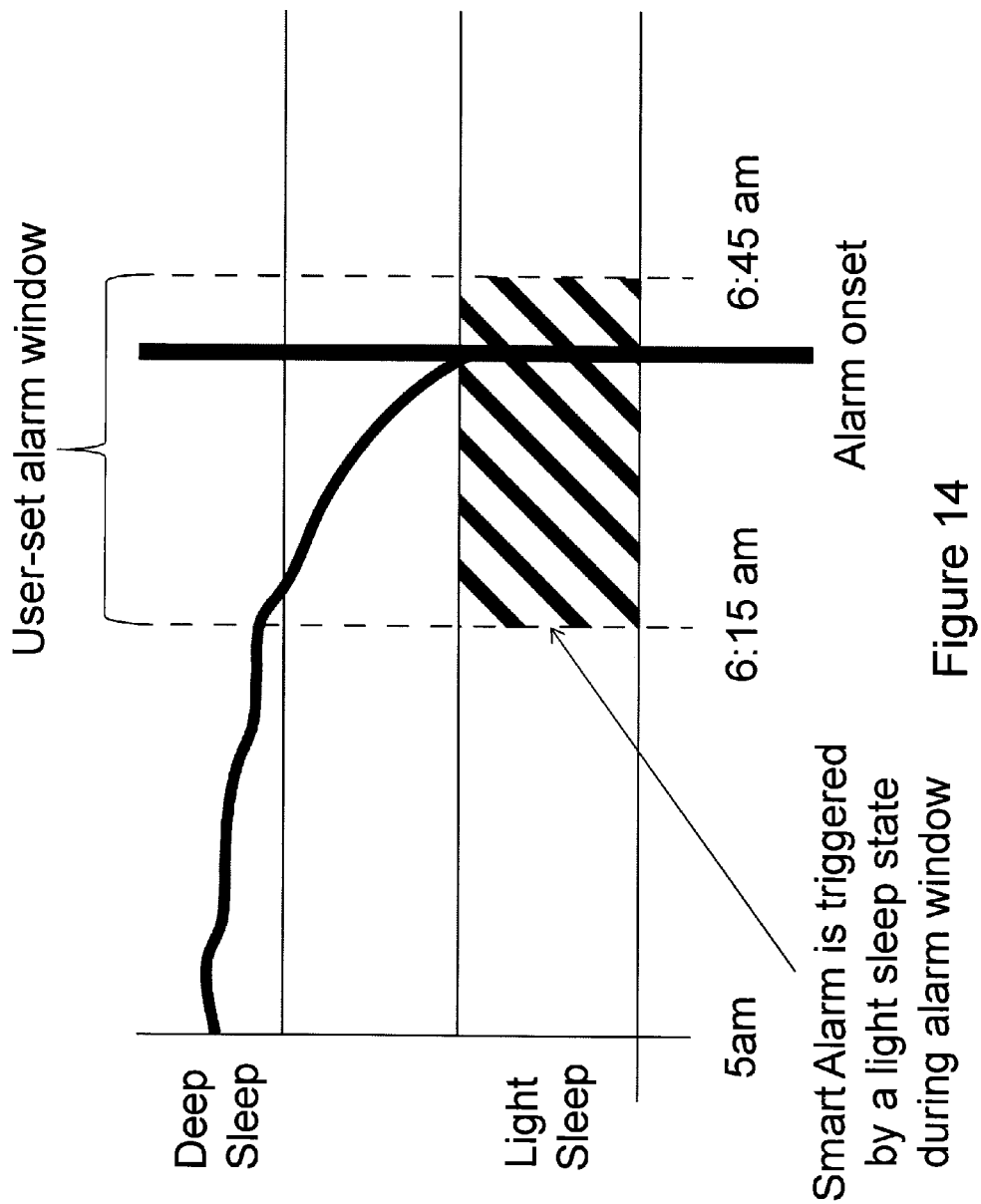
FIG. 14 illustrates functionality of a portable biometric monitoring device smart alarm feature wherein, in this embodiment, the monitoring device may be able to detect or may be in communication with a device which can detect the sleep stage or state of a user (e.g. light or deep sleep); the user may set a window of time which they would like to be awoken (e.g. 6:15 am to 6:45 am); the smart alarm may be triggered by the user going into a light sleep state during the alarm window.

In one embodiment, the biometric monitoring device of the present invention may act as a wrist-mounted vibrating alarm to silently wake the user from sleep. The biometric monitoring device may track the user's sleep quality, waking periods, sleep latency, sleep efficiency, sleep stages (e.g., deep sleep vs REM), and/or other sleep-related metrics through one or a combination of heart rate, heart rate variability, galvanic skin response, motion sensing (e.g., accelerometer, gyroscope, magnetometer), and skin temperature. The user may specify a desired alarm time and the invention may use one or more of the sleep metrics to determine an optimal time to wake the user. In one embodiment, when the vibrating alarm is active, the user may cause it to hibernate or turn off by slapping or tapping the device (which is detected, for example, via motion sensor(s), a pressure/force sensor and/or capacitive touch sensor in the device). In one embodiment, the device may attempt to arouse the user at an optimum point in the sleep cycle by starting a small vibration at a specific user sleep stage or time prior to the alarm setting. It may progressively increase the intensity or noticeability of the vibration as the user progresses toward wakefulness or toward the alarm setting. (See, for example, FIG. 14).

In another aspect, the biometric monitoring device may be configured or communicated with using onboard optical sensors such as the components in an optical heart rate monitor.

Wireless Connectivity and Data Transmission

The biometric monitoring device of the present invention may include a means of wireless communication to transmit and receive information from the Internet and/or other devices. The wireless communication may consist of one or more means such as Bluetooth, ANT, WLAN, power-line networking, and cell phone networks. These are provided as examples and do not exclude other wireless communication methods existent or that are yet to be invented.

The wireless connection is two ways. The device may transmit, communicate and/or push its data to other peripheral devices and/or the Internet. The device may also receive, request and/or pull data from other peripheral devices and/or the Internet.

The biometric monitoring device may act as a relay to provide communication for other devices to each other or to the Internet. For example, the device may connect to the Internet via WLAN but also be equipped with an ANT radio. An ANT device may communicate with the device to transmit its data to the Internet through the device's WLAN (and vice versa). As another example, the device may be equipped with Bluetooth. If a Bluetooth-enabled smart phone comes within reach of the device, the device may transmit data to or receive data from the Internet through the smart phone's cell phone network. Data from another device may also be transmitted to the device and stored (and vice versa) or transmitted at a later time.

The present invention may also include streaming or transmitting web content for displaying on the biometric monitoring device. The following are typical examples:

TABLE

1. Historical graphs of heart rate and/or other data measured by the device but stored remotely
2. Historical graphs of user activity and/or foods consumed and/or sleep data that are measured by other devices and/or stored remotely (e.g., fitbit.com)
3. Historical graphs of other user-tracked data stored remotely. Examples include heart rate, blood pressure, arterial stiffness, blood glucose levels, cholesterol, duration of TV watching, duration of video game play, mood, etc.
4. Coaching and/or dieting data based on one or more of the user's heart rate, current weight, weight goals, food intake, activity, sleep, and other data.
5. User progress toward heart rate, weight, activity, sleep, and/or other goals.
6. Summary statistics, graphics, badges, and/or metrics (e.g., "grades") to describe the aforementioned data
7. The aforementioned data displayed for the user and his/her "friends" with similar devices and/or tracking methods
8. Social content such as Twitter feeds, instant messaging, and/or Facebook updates
9. Other online content such as newspaper articles, horoscopes, weather reports, RSS feeds, comics, crossword puzzles, classified advertisements, stock reports, and websites
10. Email messages and calendar schedules Content may be delivered to the biometric monitoring device according to different contexts. For instance, in the morning, news and weather reports may be displayed along with the user's sleep data from the previous night. In the evening, a daily summary of the day's activities may be displayed.

The invention may also include NFC, RFID, or other short-range wireless communication circuitry that may be used to initiate functionality in other devices. For instance, the invention may be equipped with an NFC antenna so that when a user puts it into close proximity with a mobile phone, an app is launched automatically on the mobile phone.

These examples are provided for illustration and are not intended to limit the scope of data that may be transmitted, received, or displayed by the device, nor any intermediate processing that may occur during such transfer and display. In view of this disclosure/application, many other data can be envisioned by one reasonably skilled in the art.

Charging and Data Transmission

The biometric monitoring device may use a wired connection to charge an internal rechargeable battery and/or transfer data to a host device such as a laptop or mobile phone. In one embodiment, the device may use magnets to help the user align the device to the dock or cable. The magnetic field of magnets in the dock or cable and the magnets in the device itself could be strategically oriented to as to force the device to self align and provide a force that holds the device to the dock or cable. The magnets may also be used as conductive contacts for charging or data transmission. In another embodiment, a permanent magnet is only used in the dock or cable side, not in the device itself. This may improve the performance of the biometric monitoring device where the device employs a magnetometer. With a magnet in the device, the strong field of a nearby permanent magnet may increase the difficulty for the magnetometer to accurately measure the earth's magnetic field.

In another embodiment, the device could contain one or more electromagnets in the device body. The charger or dock for charging and data transmission would also contain an electromagnet and/or a permanent magnet. The device could only turn on its electromagnet when it is close to the charger or dock. It could detect proximity to the dock by looking for the magnetic field signature of a permanent magnet in the charger or dock using a magnetometer. Alternatively it could detect proximity to the charger by measuring the Received Signal Strength Indication or RSSI of a wireless signal from the charger or dock. The electromagnet could be reversed, creating a force that repels the device from the charging cable or dock either when the device doesn't need to be charged, synced, or when it has completed syncing or charging.

Configurable App Functionality

In some embodiments, the biometric monitoring device of the present invention may include a watch-like form factor and/or bracelet, armlet, or anklet form factor and may be programmed with "apps" that launch specific functionality and/or display specific information. Apps may be launched or closed by a variety of means including but not limited to pressing a button, using a capacitive touch sensor, performing a gesture that is detected by an accelerometer, moving to a location detected by a GPS or motion sensor, compressing the device body, thereby creating a pressure signal inside the device that is detected by an altimeter, or placing the device close to an NFC tag which is associated with an app or set of apps. Apps may also be automatically triggered to launch or close by certain environmental or physiological conditions including but not limited to a high heart rate, the detection of water using a wet sensor (to launch a swimming application for example), a certain time of day (to launch a sleep tracking application at night for example), a change in pressure and motion characteristic of a plane taking off or landing to launch and close an "airplane" mode app. Apps may also be launched or closed by meeting multiple conditions simultaneously. For example, if an accelerometer detects that a user is running and the user presses a button it may launch a pedometer application, an altimeter data collection application and/or display. In another case where the accelerometer detects swimming and the user presses the same button, it may launch a lap counting application.

In one embodiment, the device could have a swim-tracking mode that may be launched by starting a swimming app. In this mode, the device's motion sensors and/or magnetometer may be used to detect swim strokes, classify swim stroke types, detect swimming laps, and other related metrics such as stroke efficiency, lap time, speed, distance, and calorie burn. Directional changes indicated by the magnetometer may be used to detect a diversity of lap turn methods. In a preferred embodiment, data from a motion sensor and/or pressure sensor may be used to detect strokes.

In another embodiment, a bicycling app may be launched by moving the device within proximity of an NFC or RFID tag that is located on the bicycle, on a mount on the bicycle or in a location associated with a bicycle including but not limited to a bike rack or bike storage facility. (See, for example, FIG. 16). The app launched may use a different algorithm than is normally used to determine metrics including but not limited to calories burned, distance travelled, and elevation gained. The app may also be launched when a wireless bike sensor is detected including but not limited to a wheel sensor, GPS, cadence sensor, or power meter. The device may then display and/or record data from the wireless bike sensor or bike sensors.

Additional apps include but are not limited to a programmable or customizable watch face, stop watch, music player controller (e.g., mp3 player remote control), text message and/or email display or notifier, navigational compass, bicycle computer display (when communicating with a separate or integrated GPS device, wheel sensor, or power meter), weight lifting tracker, sit-up reps tracker, pull up reps tracker, resistance training form/workout tracker, golf swing analyzer, tennis (or other racquet sport) swing/serve analyzer, tennis game swing detector, baseball swing analyzer, ball throw analyzer (e.g., football, baseball), organized sports activity intensity tracker (e.g., football, baseball, basketball, volleyball, soccer), disk throw analyzer, food bite detector, typing analyzer, tilt sensor, sleep quality tracker, alarm clock, stress meter, stress/relaxation biofeedback game (e.g., potentially in combination with a mobile phone that provides auditory and/or visual cues to train user breathing in relaxation exercises), teeth brushing tracker, eating rate tracker (e.g., to count or track the rate and duration by which a utensil is brought to the mouth for food intake), intoxication or suitability to drive a motor vehicle indicator (e.g., through heart rate, heart rate variability, galvanic skin response, gait analysis, puzzle solving, and the like), allergy tracker (e.g., using galvanic skin response, heart rate, skin temperature, pollen sensing and the like, possibly in combination with external seasonal allergen tracking from, for instance, the internet; possibly determining the user's response to particular forms of allergen (e.g., tree pollen) and alerting the user to the presence of such allergens (e.g., from seasonal information, pollen tracking databases, or local environmental sensors in the device or employed by the user)), fever tracker (e.g., measuring the risk, onset, or progress of a fever, cold, or other illness, possibly in combination with seasonal data, disease databases, user location, and/or user provided feedback to assess the spread of a particular disease (e.g., flu) in relation to a user, and possibly prescribing or suggesting the abstinence of work or activity in response), electronic games, caffeine affect tracker (e.g., monitoring the physiologic response such as heart rate, heart rate variability, galvanic skin response, skin temperature, blood pressure, stress, sleep, and/or activity in either short term or long term response to the intake or abstinence of coffee, tea, energy drinks and/or other caffeinated beverages), drug affect tracker (e.g., similar to the previously mentioned caffeine tracker but in relation to other interventions, whether they be medical or lifestyle drugs such as alcohol, tobacco, etc.), endurance sport coach (e.g., recommending or prescribing the intensity, duration, or profile of a running/bicycling/swimming workout, or suggesting the abstinence or delay of a workout, in accordance with a user specified goal such as a marathon, triathlon, or custom goal utilizing data from, for instance, historical exercise activity (e.g., distance run, pace), heart rate, heart rate variability, health/sickness/stress/fever state), weight and/or body composition, blood pressure, blood glucose, food intake or caloric balance tracker (e.g., notifying the user how many calories he may consume to maintain or achieve a weight), pedometer, and nail biting detector. In some cases, the apps may rely solely on the processing power and sensors of the invention. In other cases, the apps may fuse or merely display information from an external device or set of external devices including but not limited to a heart rate strap, GPS distance tracker, body composition scale, blood pressure monitor, blood glucose monitor, watch, smart watch, mobile communication device such as a smart phone or tablet, or server.

In one embodiment, the device may control a music player on a secondary device. Aspects of the music player that may be controlled include but are not limited to the volume, selection of tracks and/or playlists, skipping forward or backward, fast forwarding or rewinding of tracks, the tempo of the track, and the music player equalizer. Control of the music player may be via user input or automatic based on physiological, environmental, or contextual data. For example, a user may be able to select and play a track on their smart phone by selecting the track through a user interface on the device. In another example, the device may automatically choose an appropriate track based on the activity level of the user (the activity level being calculated from device sensor data). This may be used to help motivate a user to maintain a certain activity level. For example, if a user goes on a run and wants to keep their heart rate in a certain range, the device may play an upbeat or higher tempo track if their heart rate is below the range which they are aiming for.

There are many inventions described and illustrated herein. While certain embodiments, features, attributes and advantages of the inventions have been described and illustrated, it should be understood that many others, as well as different and/or similar embodiments, features, attributes and advantages of the present inventions, are apparent from the description and illustrations. As such, the above embodiments of the inventions are merely exemplary. They are not intended to be exhaustive or to limit the inventions to the precise forms, techniques, materials and/or configurations disclosed. Many modifications and variations are possible in light of this disclosure. It is to be understood that other embodiments may be utilized and operational changes may be made without departing from the scope of the present inventions. As such, the scope of the inventions is not limited solely to the description above because the description of the above embodiments has been presented for the purposes of illustration and description.

Importantly, the present invention is neither limited to any single aspect nor embodiment, nor to any combinations and/or permutations of such aspects and/or embodiments. Moreover, each of the aspects of the present invention, and/or embodiments thereof, may be employed alone or in combination with one or more of the other aspects and/or embodiments thereof. For the sake of brevity, many of those permutations and combinations will not be discussed and/or illustrated separately herein.

Accordingly, the present embodiments are to be considered as illustrative and not restrictive, and the various embodiments described in the present disclosure are not to be limited to the details given herein, but may be modified within the scope and equivalents of the appended claims.

What is claimed is:

1. An activity monitoring device, comprising,
a housing configured for attachment to a body part of a user;
a display screen attached to the housing;
a sensor for capturing physiological conditions of the user, the sensor being disposed along a surface of the housing so that the sensor is proximate to the body part, the body part having at least some exposed skin;
memory for storing the captured physiological conditions; and
a processor for examining the captured physiological conditions, and at a particular time, automatically selecting an application to execute from a plurality of applications based on characteristics of the captured physiological conditions;
wherein the plurality of applications are stored in memory of the activity monitoring device and the processor executes instructions for the automatic selection of the application,
wherein the processor selects one of a plurality of applications including a watch function, or a pedometer function, or a communication function, or a biometric analysis function, or a sleep tracking function, or a calendar function, or an environmental analysis function, or a geo-location function, or a mapping function, or a heart rate analysis function, or a sedentary tracking function, or a motion data analysis function, or a combination of two or more thereof.

2. The activity monitoring device of claim 1, wherein the sensor includes a plurality of light emitting devices and at least one detector.

3. The activity monitoring device of claim 1, wherein the captured physiological conditions include a heart rate of the user.

4. The activity monitoring device of claim 1, wherein the sensor includes a plurality of light emitting devices (LEDs) and at least one detector, wherein the LEDs are directed toward the exposed skin of the user.

5. The activity monitoring device of claim 1, wherein the housing includes a band for enabling the attachment to the body part of the user.

6. The activity monitoring device of claim 1, wherein the housing includes a wrist band and the body part of the user includes a wrist of the user, and the surface of the housing is configured to be proximate to the skin of the user.

7. The activity monitoring device of claim 1, further comprising, an environmental sensor for capturing environment data, the processor configured to execute the automatic selection additionally based on based on the environment data.

8. The activity monitoring device of claim 1, wherein automatically selecting the application to execute causes data to be processed and stored in the memory and/or data to be displayed on the display screen.

9. The activity monitoring device of claim 1, wherein automatically selecting the application to execute includes launching a specific functionality provided by the selected application.

10. The activity monitoring device of claim 1, wherein the processor is further configured to automatically close the application in response to examining the physiological conditions and environmental conditions.

11. The activity monitoring device of claim 1, wherein the processor is further configured to set one or more modes of one or more applications of the activity monitoring device based on examination of the physiological conditions and/or environmental conditions.

12. An activity monitoring device, comprising, a wrist band; a display screen disposed on a housing, the wrist band being coupled to the housing; a sensor disposed in the housing to capture data associated with a user; memory disposed in the housing for storing the captured data and for storing one or more applications; and a processor in communication with the housing and the display screen, the processor configured to automatically select for execution execute the one or more applications of a plurality of applications for rendering to render content associated with the one or more applications on the display screen, at least one of the applications being configured to present metrics regarding the captured data of the sensor, the captured data including one of motion data by the user, environmental data, biometric data of the user, or combinations of two or more thereof, the processor enabling user access to the one or more applications wherein the plurality of applications are stored in memory of the activity monitoring device and the processor executes instructions for the automatic selection of the application, wherein the processor selects one of a plurality of applications including a watch function, or a pedometer function, or a communication function, or a biometric analysis function, or a sleep tracking function, or a calendar function, or an environmental analysis function, or a geo-location function, or a mapping function, or a heart rate analysis function, or a sedentary tracking function, or a motion data analysis function, or a combination of two or more thereof; and wherein the processor is configured to cause rendering of a user interface on the display screen wherein the automatic selection is based on characteristics of the captured data.

13. An activity monitoring device of claim 12, wherein one of the applications provides a watch function, a pedometer function, a communication function, a biometric analysis function, an environmental conditions analysis function, a motion data analysis function, or combinations thereof.

14. The activity monitoring device of claim 12, wherein the sensor includes a plurality of light emitting devices and at least one detector.

15. The activity monitoring device of claim 12, wherein the biometric data provides at least one physiological condition of the user.

16. The activity monitoring device of claim 15, wherein the physiological condition is a heart rate of the user.

17. The activity monitoring device of claim 12, wherein the sensor includes a plurality of light emitting devices (LEDs) and at least one detector, wherein the LEDs are directed toward the exposed skin of the user.

\* \* \* \* \*

UNITED STATES PATENT AND TRADEMARK OFFICE
CERTIFICATE OF CORRECTION

PATENT NO. : 9,241,635 B2
APPLICATION NO. : 14/156413
DATED : January 26, 2016
INVENTOR(S) : Shelten Gee Jao Yuen et al.

Page 1 of 1

It is certified that error appears in the above-identified patent and that said Letters Patent is hereby corrected as shown below:

On the Title Page

Item (72), Lines 5-6, the text "Andrew Cole Axely" should be canceled and replaced with "--Andrew Cole Axley--".

In the Claims

Claim 12, Column 34, Line 59, the text "execute the" should be canceled.
Claim 12, Column 34, Lines 60-61, the text "to render" should be canceled.
Claim 12, Column 34, Line 67, the text "--,--" should be inserted in between "applications" and "wherein".
Claim 12, Column 35, Line 12, the text "; and" should be canceled and the text "--,--" inserted in its place.
Claim 12, Column 35, Line 14, the text "--, and--" should be inserted in between "screen" and "wherein".

Signed and Sealed this
Sixteenth Day of June, 2020

Andrei Iancu
*Director of the United States Patent and Trademark Office*